(12) United States Patent
Thomas et al.

(10) Patent No.: US 11,946,039 B2
(45) Date of Patent: Apr. 2, 2024

(54) CLASS II, TYPE II CRISPR SYSTEMS

(71) Applicant: Metagenomi, Inc., Emeryville, CA (US)

(72) Inventors: Brian Thomas, Emeryville, CA (US); Christopher Brown, Emeryville, CA (US); Audra Devoto, Emeryville, CA (US); Cristina Butterfield, Emeryville, CA (US); Lisa Alexander, Emeryville, CA (US); Daniela S. A. Goltsman, Emeryville, CA (US)

(73) Assignee: Metagenomi, Inc., Emeryville, CA (US)

( * ) Notice: Subject to any disclaimer, the term of this patent is extended or adjusted under 35 U.S.C. 154(b) by 0 days.

(21) Appl. No.: 17/857,923

(22) Filed: Jul. 5, 2022

(65) Prior Publication Data

US 2023/0051396 A1 Feb. 16, 2023

Related U.S. Application Data

(63) Continuation of application No. PCT/US2021/024945, filed on Mar. 30, 2021.

(60) Provisional application No. 63/116,149, filed on Nov. 19, 2020, provisional application No. 63/003,159, filed on Mar. 31, 2020.

(51) Int. Cl.
| | |
|---|---|
| *C12N 15/10* | (2006.01) |
| *C12N 9/22* | (2006.01) |
| *C12N 9/78* | (2006.01) |
| *C12N 15/11* | (2006.01) |
| *C12N 15/63* | (2006.01) |

(52) U.S. Cl.
CPC ............ *C12N 15/102* (2013.01); *C12N 9/22* (2013.01); *C12N 9/78* (2013.01); *C12N 15/11* (2013.01); *C12N 15/63* (2013.01); *C12N 2310/20* (2017.05)

(58) Field of Classification Search
None
See application file for complete search history.

(56) References Cited

U.S. PATENT DOCUMENTS

| | | |
|---|---|---|
| 5,858,988 A | 1/1999 | Wang |
| 6,291,438 B1 | 9/2001 | Wang |
| 8,889,418 B2 | 11/2014 | Zhang et al. |
| 10,011,849 B1 | 7/2018 | Gill et al. |
| 10,392,607 B2 | 8/2019 | Sternberg et al. |
| 10,913,941 B2 | 2/2021 | Thomas et al. |
| 10,982,200 B2 | 4/2021 | Thomas et al. |
| 2014/0186919 A1 | 7/2014 | Zhang et al. |
| 2014/0186958 A1 | 7/2014 | Zhang et al. |
| 2015/0045546 A1 | 2/2015 | Siksnys et al. |
| 2016/0289700 A1 | 10/2016 | Barrangou et al. |
| 2016/0362667 A1 | 12/2016 | Donohoue et al. |
| 2018/0371498 A1 | 12/2018 | Gill et al. |
| 2019/0010471 A1 | 1/2019 | Zhang et al. |
| 2019/0249200 A1 | 8/2019 | Seebeck et al. |
| 2019/0264232 A1 | 8/2019 | Hou et al. |
| 2020/0080067 A1 | 3/2020 | Zhang et al. |
| 2020/0332273 A1 | 10/2020 | Thomas et al. |
| 2022/0033791 A1 | 2/2022 | Thomas et al. |
| 2022/0220460 A1 | 7/2022 | Thomas et al. |
| 2022/0298494 A1 | 9/2022 | Thomas et al. |
| 2022/0403357 A1* | 12/2022 | Zhang ............ C12Y 305/04004 |

FOREIGN PATENT DOCUMENTS

| | | |
|---|---|---|
| CA | 3091267 A1 | 8/2019 |
| CN | 104520429 A | 4/2015 |
| CN | 105142669 A | 12/2015 |
| CN | 105209621 A | 12/2015 |
| EP | 3141604 A1 | 3/2017 |
| EP | 3617311 A1 | 3/2020 |
| WO | WO-2015066119 A1 | 5/2015 |
| WO | WO-2016073990 A2 | 5/2016 |
| WO | WO-2016141224 A1 | 9/2016 |
| WO | WO-2016186953 A1 | 11/2016 |
| WO | WO-2017155714 A1 | 9/2017 |
| WO | WO-2018035250 A1 | 2/2018 |
| WO | WO-2018074979 A1 | 4/2018 |
| WO | WO-2018172556 A1 | 9/2018 |
| WO | WO-2018209712 A1 | 11/2018 |
| WO | WO-2019161290 A1 | 8/2019 |
| WO | WO-2020055941 A1 | 3/2020 |
| WO | WO-2020168234 A1 | 8/2020 |
| WO | WO-2020168291 A1 | 8/2020 |
| WO | WO-2020236967 A1 | 11/2020 |
| WO | WO-2021097118 A1 | 5/2021 |
| WO | WO-2021202559 A1 | 10/2021 |
| WO | WO-2021202568 A1 | 10/2021 |
| WO | WO-2021226363 A1 | 11/2021 |
| WO | WO-2021226369 A1 | 11/2021 |

(Continued)

OTHER PUBLICATIONS

Kapitonov et al., "ISC, a Novel Group of Bacterial and Archaeal DNA Transposons That Encode Cas9 Homologs" 198(5) Journal of Bacteriology 797-807 (Year: 2015).*

Ding et al.: Recent Advances in Genome Editing Using CRISPR/Cas9. Front Plant Sci. 7:703:1-12 doi:10.3389/fpls.2016.00703 (2016).

Andronescu et al. Efficient Parameter Estimation for RNA Secondary Structure Prediction. Bioinformatics 23(13):119-28 (2007).

Burstein et al.: New CRISPR-Cas systems from uncultivated microbes. Nature. 542(7640):237-241 (2017).

CtSkennerton: Mining CRISPRs in Environmental Datasets: Minced. GitHub URL:www.github.com/ctSkennerton/minced [1-4](2019).

Gasiunas et al. Cas9-crRNA ribonucleoprotein complex mediates specific DNA cleavage for adaptive immunity in bacteria. PNAS 109:E2579-2586 (2012).

(Continued)

*Primary Examiner* — Nancy J Leith
(74) *Attorney, Agent, or Firm* — Wilson Sonsini Goodrich & Rosati

(57) ABSTRACT

The present disclosure provides for endonuclease enzymes as well as methods of using such enzymes or variants thereof.

24 Claims, 21 Drawing Sheets

Specification includes a Sequence Listing.

(56) References Cited

FOREIGN PATENT DOCUMENTS

WO    WO-2022087494 A1    4/2022

OTHER PUBLICATIONS

Herdewijn: Heterocyclic modifications of oligonucleotides and antisense technology. Antisense & Nucleic Acid Drug Dev 10:297-310 (2000).
Huber et al. Orchestrating High-Throughput Genomic Analysis With Bioconductor. Nat Methods 12(2):115-21 (2015).
Jinek et al. A programmable dual-RNA-guided DNA endonuclease in adaptive bacterial immunity. Science 337(6096):816-821 (2012).
Karvelis et al. Methods for Decoding Cas9 Protospacer Adjacent Motif (PAM) Sequences: A Brief Overview. Methods 121-122:3-8 (2017).
Mali et al. RNA-guided human genome engineering via Cas9. Science 339(6121):823-826 (2013).
Mir et al.: Type II-C CRISPR-Cas9 Biology, Mechanism, and Application. ACS Chem Biol. 13(2):357-365 (2018).
Moon et al.: Recent advances in the CRISPR genome editing tool set. Exp Mol Med. 51(11):1-11 (2019).
NCBI GenBank Accession No. HHR99113.1, TPA: type II CRISPR RNA-guided endonuclease Cas9 [*Acidobacteria bacterium*] [1-2](2020).
NCBI GenBank Accession No. WP_061212298.1, HNH endonuclease [*Dermabacter hominis*] [1-2](2016).
NCBI Reference Sequence: RMH36335.1, hypothetical protein D66910_06140 [*Nitrospirae bacterium*], https://www.ncbi.nlm.nih.gov/protein/RMH36335.1/ [1-2](Published on Oct. 29, 2018).
PCT/US2020/018353 International Search Report and Written Opinion dated Jun. 30, 2020.
PCT/US2020/018432 International Search Report and Written Opinion dated Jun. 30, 2020.
PCT/US2021/024927 International Search Report and Written Opinion dated Jul. 21, 2021.
PCT/US2021/024945 International Search Report and Written Opinion dated Jul. 20, 2021.
PCT/US2021/031136 International Search Report and Written Opinion dated Aug. 25, 2021.
PCT/US2021/031143 International Search Report and Written Opinion dated Aug. 25, 2021.
Rautela et al.: Efficient genome editing of human natural killer cells by CRISPR RNP. bioRxiv prePrint doi: https://doi.org/10.1101/406934 [1-24] (2018).
Schneider et al. Sequence logos: a new way to display consensus sequences. Nucleic acids research 18(20):6097-6100 (1990).
Shmakov et al. Discovery and Functional Characterization of Diverse Class 2 CRISPR-Cas Systems. Mol Cell 60(3):385-397 (2015).
Shmakov, et al.: Diversity and evolution of class 2 CRISPR-Cas systems. Nature Reviews Microbiology 15(3): 169-182 (2017).
Tang et al.: Class 2 CRISPR/Cas: an expanding biotechnology toolbox for and beyond genome editing. Cell Biosci. 8:59 doi:10.1186/s13578-018-0255-x [1-13](2018).
Tareen et al.: Logomaker: beautiful sequence logos in Python. Bioinformatics 6(7):2272-2274 (2020).
U.S. Appl. No. 16/917,837 Office Action dated Aug. 26, 2020.
U.S. Appl. No. 16/917,838 Office Action dated Jul. 28, 2020.
Koonin et al. (2017) Diversity, classification and evolution of CRISPR-Cas systems. Current Opinion in Microbiology, 37:67-78 (Year : 2017).
Uniprotkb/trembl: A0A1FOKNW4 • A0A1F0KNW4_9MICC HNHc domain-containing protein. *Rothia* sp. HMSC066H02, pp. 1-5 [retrieved online Dec. 1, 2022] URL: https://www.uniprot.org/uniprotkb/A0A1F0KNW4/entry (Feb. 15, 2017).
Uniprotkb/trembl: A0A1S1DAD0 • A0A1S1DAD0_9MICC HNH Cas9-type domain-containing protein. *Rothia* sp. HMSC065C03, pp. 1-5 [retrieved online Dec. 1, 2022] URL: https://www.uniprot.org/uniprotkb/A0A1S1DAD0/entry (Apr. 12, 2017).
Uniprotkb/trembl: A1F0PN46 • A0A1F0PN46_9MICC HNH Cas9-type domain-containing protein. *Rothia* sp. HMSC076D04, pp. 1-5 [retrieved online Dec. 1, 2022] URL: https://www.uniprot.org/uniprotkb/A0A1F0PN46/entry (Feb. 15, 2017).
Goltsman et al.: Compact Cas9d and HEARO enzymes for genome editing discovered from uncultivated microbes. Nat Commun. 13(1):7602:1-11. doi:10.1038/s41467-022-35257-7 (2022).
U.S. Appl. No. 17/193,173 Final Office Action dated Apr. 17, 2023.
Fang et al.: CRISPR/Cas9-mediated Genome Editing Technology. Progress in Biochemistry and Biophysics, 40(8):691-702 [with English Machine Translation] (2013).
Guo et al.: Off-target effects and optimization strategies of CRISPR/Cas9 technology. Progress in Biochemistry and Biophysics, 45(8):798-807 [with English Machine Translation] (2018).
NCBI GenBank: GBR72910.1—CRISPR-associated protein Csn1 family [*Candidatus Termititenax aidoneus*], pp. 1-3 (Oct. 31, 2019).
NCBI GenBank: WP_070675185.1—Multispecies: HNH endonuclease [unclassified Rothia (in: high G+C Gram-positive bacteria)], pp. 1-2 (Jan. 20, 2023).
NCBI GenBank: WP_070690139.1—HNH endonuclease [*Rothia* sp. HMSC076D04], pp. 1-3 (Jan. 20, 2023).
NCBI GenBank: WP_070847477.1—HNH endonuclease [*Rothia* sp. HMSC065C03], pp. 1-2 (May 16, 2022).
Altae-Tran et al.: The widespread IS200/IS605 transposon family encodes diverse programmable RNA-guided endonucleases. Science. 374(6563):57-65 doi:10.1126/science.abj6856 (2021).
Bitard-Feildel,T. et al., "Order in Disorder as Observed by the Hydrophobic Cluster Analysis of Protein Sequences", Proteomics, 2018, vol. 18, E1800054, pp. 1-12.
Carugo, O., Amino Acid Composition and Protein Dimension, Protein Science, Oct. 2008, vol. 17, No. 12, pp. 2187-2191.
Co-pending U.S. Appl. No. 18/053,232, inventors Thomas; Brian et al., filed Nov. 7, 2022.
Dyson, H.J., "Roles of intrinsic disorder in protein-nucleic acid interactions", Mol Biosyst, 2011, vol. 8, No. 1, pp. 97-104.
Gasiunas, G. et al, "A catalogue of biochemically diverse CRISPR-Cas9 orthologs", Nat Commun, 2020, vol. 11, No. 5512, pp. 1-10.
Harms, M. et al., "Analyzing protein structure and function using ancestral gene reconstruction", Current Opinion in Structural Biology, 2010, vol. 20, No. 6, pp. 360-366.
Harris, K.A. et al., "Large Noncoding RNAs in Bacteria", Microbiol Spectr, 2018, vol. 6, No. 4, pp. 1-18.
Katoh, K. et al., "MAFFT Multiple Sequence Alignment Software Version 7: Improvements in Performance and Usability", Molecular Biology and Evolution, 2013, vol. 30, No. 4, pp. 772-780.
Madshus, I.H.. "Regulation of intracellular pH in eukaryotic cells", Biochemical Journal, 1988, vol. 250, No. 1, pp. 1-8.
Murthy, A.C. et al., "Molecular interactions underlying liquid-liquid phase separation of the FUS low complexity domain", Nat Struct Mol Biol, 2019, vol. 26, No. 7, pp. 637-648.
Osorio, D. et al., "Peptides: A Package for Data Mining of Antimicrobial Peptides", The R. Journal, 2015, 7(1), 4-14, pp. 1-11.
Price, M.N. et al., "Fast Tree2—Approximately Maximum-Likelihood Trees for Large Alignments", PLOS One, 2010, vol. 5, No. 3, e9490, pp. 1-10.
Stamatakis, A., "Raxml Version 8: a tool for phylogenetic analysis and post-analysis of large phylogenies", Bioinformatics, 2014, vol. 30, No. 9, pp. 1312-1313.
Weinberg, Z. et al, "Extraordinary Structured Noncoding RNAs Revealed by Bacterial Metagenome Analysis", Nature 2009, vol. 462, No. 7273, pp. 656-659.
Xiao, N. et la., "protr/ProtrWeb: R package and web server for generating various numerical representation schemes of protein sequences", Bioinformatics, 2015, vol. 31, No. 11, pp. 1857-1859.
Yang, Z., "PAML 4: Phylogenetic Analysis by Maximum Likelihood", Molecular Biology and Evolution, 2007, vol. 24, No. 8, pp. 1586-1591.

\* cited by examiner

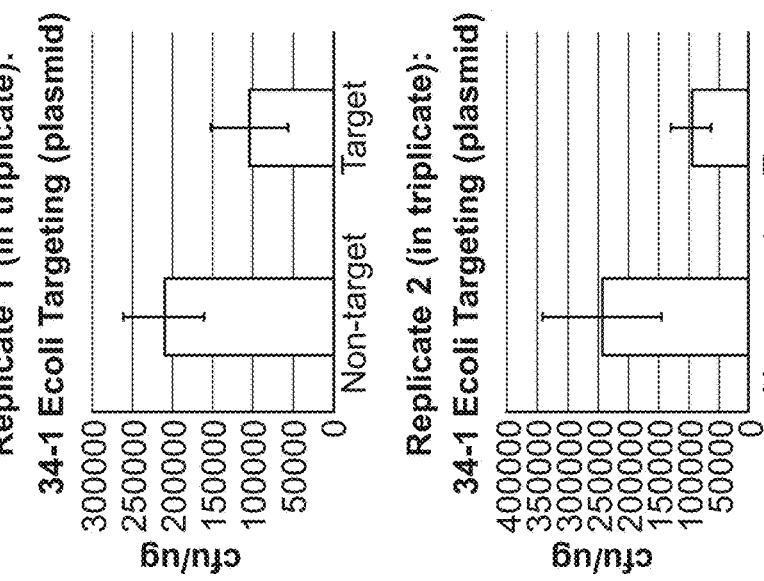
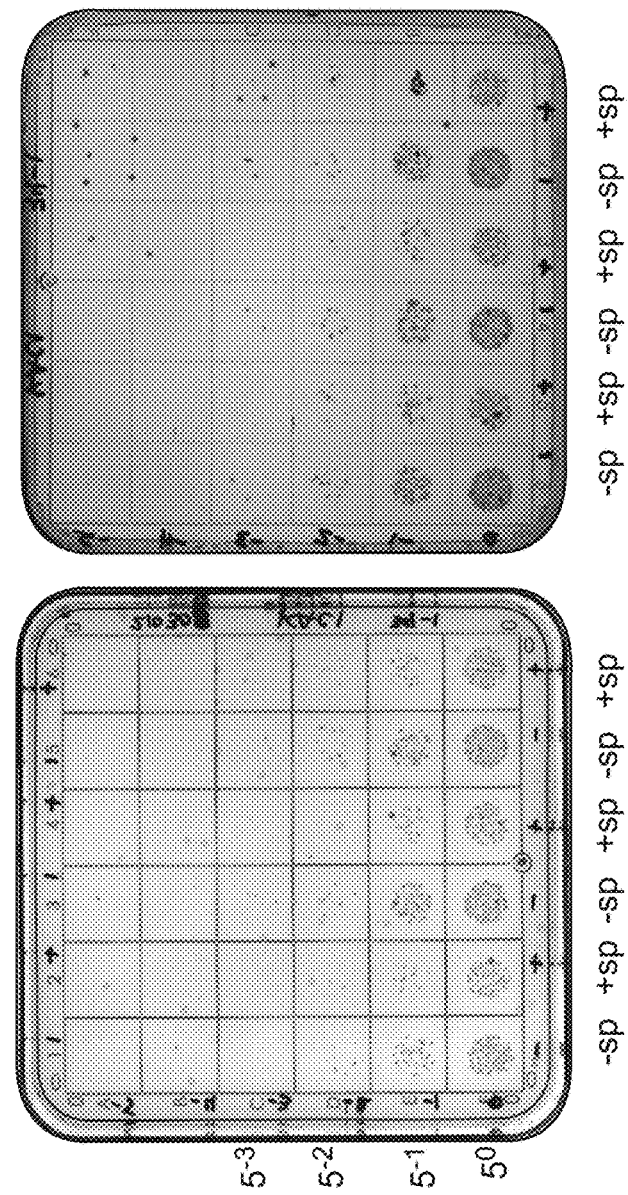
FIG. 12A
FIG. 12B

CLASS II, TYPE II CRISPR SYSTEMS

CROSS-REFERENCE

This application is a continuation application of International Application No. PCT/US2021/024945, entitled "CLASS II, TYPE II CRISPR SYSTEMS", filed Mar. 30, 2021, which claims the benefit of U.S. Provisional Application No. 63/116,149, entitled "CLASS II, TYPE II CRISPR SYSTEMS", filed on Nov. 19, 2020, and U.S. Provisional Application No. 63/003,159, entitled "CLASS II, TYPE II CRISPR SYSTEMS", filed on Mar. 31, 2020, each of which applications is incorporated in its entirety herein.

SEQUENCE LISTING

The instant application contains a Sequence Listing which has been submitted electronically in XML format and is hereby incorporated by reference in its entirety. Said XML copy, created on Apr. 29, 2023, is named 55921-711_301 v4.xml and is 1,618,142 bytes in size.

BACKGROUND

Cas enzymes along with their associated Clustered Regularly Interspaced Short Palindromic Repeats (CRISPR) guide ribonucleic acids (RNAs) appear to be a pervasive (~45% of bacteria, ~84% of archaea) component of prokaryotic immune systems, serving to protect such microorganisms against non-self nucleic acids, such as infectious viruses and plasmids by CRISPR-RNA guided nucleic acid cleavage. While the deoxyribonucleic acid (DNA) elements encoding CRISPR RNA elements may be relatively conserved in structure and length, their CRISPR-associated (Cas) proteins are highly diverse, containing a wide variety of nucleic acid-interacting domains. While CRISPR DNA elements have been observed as early as 1987, the programmable endonuclease cleavage ability of CRISPR/Cas complexes has only been recognized relatively recently, leading to the use of recombinant CRISPR/Cas systems in diverse DNA manipulation and gene editing applications. Owing to the utility of these enzymes, they are being repurposed for a wide variety of biotechnology, gene editing, and therapeutic applications. Due to their single-effector architecture, the majority of systems currently being repurposed for genome engineering belong to the CRISPR Class 2, Type II and Class 2, Type V categories.

SUMMARY

The large size (greater than ca. 1200 amino acids) of many class 2 Cas effectors makes delivery for therapeutic applications challenging. Accordingly, described herein are methods, compositions, and systems relating to novel putative guided dsDNA nucleases referred to as SMART (SMall ARchaeal-associaTed) nuclease systems. These endonuclease effectors are defined by their small size (400 aa-1050 aa), the presence of RuvC and HNH catalytic domains, and other predicted protein features that together suggest novel biochemical mechanisms.

In some aspects, the present disclosure provides for an engineered nuclease system, comprising: (a) an endonuclease comprising a RuvC domain and an HNH domain, wherein said endonuclease is derived from an uncultivated microorganism; and (b) an engineered guide ribonucleic acid structure configured to form a complex with said endonuclease comprising: (i) a guide ribonucleic acid sequence configured to hybridize to a target deoxyribonucleic acid sequence; and (ii) a tracr ribonucleic acid sequence configured to bind to said endonuclease; wherein said endonuclease has a molecular weight of about 96 kDa or less. In some embodiments, said endonuclease is an archaeal endonuclease. In some embodiments, said endonuclease is a Class 2, Type II Cas endonuclease. In some embodiments, said endonuclease comprises a sequence with at least 70%, at least 75%, at least 80% or at least 90% sequence identity to any one of SEQ ID NOs: 1-198, 221-459, 463-612, or 617-668. In some embodiments, said endonuclease further comprises an arginine-rich region comprising an RRxRR motif or a domain with PF14239 homology. In some embodiments, said arginine rich region or said domain with PF14239 homology has at least 85%, at least 90%, or at least 95% identity to an arginine rich region or a domain with PF14239 homology of any one of SEQ ID NOs: 1-198, 221-459, 463-612, or 617-668. In some embodiments, said endonuclease further comprises a REC (recognition) domain. In some embodiments, said REC domain has at least 85%, at least 90%, or at least 95% identity to a REC domain of any one of SEQ ID NOs: 1-198, 221-459, 463-612, or 617-668. In some embodiments, said endonuclease further comprises a BH (bridge helix) domain, a WED (wedge) domain, and a PI (PAM interacting) domain. In some embodiments, said BH domain, said WED domain, or said PI domain has at least 85%, at least 90%, or at least 95% identity to a BH domain, a WED domain, and/or a PI domain of any one of SEQ ID NOs: 1-198, 221-459, 463-612, or 617-668.

In some aspects, the present disclosure provides for an engineered nuclease system comprising: (a) an endonuclease comprising a RuvC-I domain and an HNH domain; and (b) an engineered guide ribonucleic acid structure configured to form a complex with said endonuclease comprising: (i) a guide ribonucleic acid sequence configured to hybridize to a target deoxyribonucleic acid sequence; and (ii) a ribonucleic acid sequence configured to bind to said endonuclease, wherein said endonuclease comprises a sequence with at least 70%, at least 75%, at least 80% or at least 90% sequence identity to any one of SEQ ID NOs: 1-198, 221-459, 463-612, or 617-668. In some embodiments, said endonuclease is an archaeal endonuclease. In some embodiments, said endonuclease is a class 2, type II Cas endonuclease. In some embodiments, said endonuclease further comprises an arginine-rich region comprising an RRxRR motif or a domain with PF14239 homology. In some embodiments, said arginine rich region or said domain with PF14239 homology has at least 85%, at least 90%, or at least 95% identity to an arginine rich region of any one of SEQ ID NOs: 1-198, 221-459, 463-612, or 617-668. In some embodiments, said endonuclease further comprises a REC (recognition) domain. In some embodiments, said REC domain having at least 85%, at least 90%, or at least 95% identity to a REC domain of any one of SEQ ID NOs: 1-198, 221-459, 463-612, or 617-668. In some embodiments, said endonuclease further comprises a BH domain, a WED domain, and a PI domain. In some embodiments, said BH domain, said WED domain, or said PI domain has at least 85%, at least 90%, or at least 95% identity to a BH domain, a WED domain, and/or a PI domain of any one of SEQ ID NOs: 1-198, 221-459, 463-612, or 617-668. In some embodiments, said endonuclease is derived from an uncultivated microorganism. In some embodiments, said ribonucleic acid sequence configured to bind said endonuclease comprises a sequence with at least 80% sequence identity to any one of SEQ ID NOs: 199-200, 460-461, or 669-673, or a sequence with at least 80% sequence identity to the non-degenerate nucleotides of any one of SEQ ID NOs: 201-203 or 613-616. In some embodiments, said guide nucleic acid structure comprises a sequence with at least 80% identity to the non-degenerate nucleotides of any one of SEQ ID NOs: 201-203, 613-616.

In some aspects, the present disclosure provides for an engineered nuclease system comprising: (a) an engineered guide ribonucleic acid structure comprising: (i) a guide ribonucleic acid sequence configured to hybridize to a target deoxyribonucleic acid sequence; and (ii) a ribonucleic acid sequence configured to bind to an endonuclease, wherein said ribonucleic acid sequence comprises a sequence with at least 80% sequence identity to any one of SEQ ID NOs: 199-200, 460-461, or 669-673, or a sequence with at least 80% sequence identity to nonvariable nucleotides of any one of SEQ ID NOs: 201-203 or 613-616; and (b) an RNA-guided endonuclease configured to bind to said engineered guide ribonucleic acid. In some embodiments, said RNA-guided endonuclease is an archaeal endonuclease. In some embodiments, said endonuclease has a molecular weight of about 120 kDa or less, 100 kDa or less, 90 kDa or less, or 60 kDa or less. In some embodiments, said engineered guide ribonucleic acid structure comprises at least two ribonucleic acid polynucleotides. In some embodiments, said engineered guide ribonucleic acid structure comprises a single ribonucleic acid polynucleotide comprising said guide ribonucleic acid sequence and said tracr ribonucleic acid sequence. In some embodiments, said guide ribonucleic acid sequence is complementary to a prokaryotic, bacterial, archaeal, eukaryotic, fungal, plant, mammalian, or human genomic sequence. In some embodiments, said guide ribonucleic acid sequence is 15-24 nucleotides in length. In some embodiments, said endonuclease comprises one or more nuclear localization sequences (NLSs) proximal to an N- or C-terminus of said endonuclease. In some embodiments, said NLS comprises a sequence selected from SEQ ID NOs: 205-220. In some embodiments, the system further comprises a single- or double-stranded DNA repair template comprising from 5' to 3': a first homology arm comprising a sequence of at least 20 nucleotides 5' to said target deoxyribonucleic acid sequence, a synthetic DNA sequence of at least 10 nucleotides, and a second homology arm comprising a sequence of at least 20 nucleotides 3' to said target sequence. In some embodiments, said first or second homology arm comprises a sequence of at least 40, 80, 120, 150, 200, 300, 500, or 1,000 nucleotides. In some embodiments, said system further comprises a source of Mg 2+. In some embodiments, said endonuclease and said tracr ribonucleic acid sequence are derived from distinct bacterial species within a same phylum. In some embodiments, said endonuclease comprises a sequence with at least 70% sequence identity to any one of SEQ ID NOs: 2-24 and said guide RNA structure comprises an RNA sequence predicted to comprise a hairpin comprising a stem and a loop, wherein said stem comprises at least 12 pairs of ribonucleotides. In some embodiments, said guide RNA structure further comprises a second stem and a second loop, wherein the second stem comprises at least 5 pairs of ribonucleotides. In some embodiments, said guide RNA structure further comprises an RNA structure comprising at least two hairpins. In some embodiments, said endonuclease comprises a sequence with at least 70% sequence identity to SEQ ID NO: 1 and said guide RNA structure comprises an RNA sequence predicted to comprise at least four hairpins comprising a stem and a loop. In some embodiments: a) said endonuclease comprises a sequence at least 70%, at least 80%, or at least 90% identical to any one of SEQ ID NOs: 1, 2, 10, 17, or 613-616; and b said guide RNA structure comprises a sequence at least 70%, at least 80%, or at least 90% identical to any one of SEQ ID NOs: 199-200 or 669-673 or the nonvariable nucleotides of any one of SEQ ID NOs: 201-203 or 613-616. In some embodiments: a) said endonuclease comprises a sequence at least 70%, at least 80%, or at least 90% identical to any one of SEQ ID NOs: 1-24, 462-488, or 501-612; and b) said guide RNA structure comprises a sequence at least 70%, at least 80%, or at least 90% identical to any one of SEQ ID NOs: 199-200 or 669-673 or the nonvariable nucleotides of any one of SEQ ID NOs: 201-203 or 613-616. In some embodiments: a)
said endonuclease comprises a sequence at least 70%, at least 80%, or at least 90% identical to any one of SEQ ID NOs: 2, 10, or 17; and b) said guide RNA structure comprises a sequence at least 70%, at least 80%, or at least 90% identical to the nonvariable nucleotides of any one of SEQ ID NOs:202-203 or 613-614. In some embodiments: a) said endonuclease comprises a sequence at least 70%, at least 80%, or at least 90% identical to any one of SEQ ID NOs: 25-198, 221-459, or 489-580; and b) said guide RNA structure comprises a sequence at least 70%, at least 80%, or at least 90% identical to a class 2, type II sgRNA or tracr sequence. In some embodiments, said sequence identity is determined by a BLASTP, CLUSTALW, MUSCLE, MAFFT, or CLUSTALW with parameters of the Smith-Waterman homology search algorithm. In some embodiments, said sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment. In some embodiments, said endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said endonuclease has less than 80% identity to a Cas9 endonuclease.

In some aspects, the present disclosure provides for an engineered single guide ribonucleic acid polynucleotide comprising: a) a DNA-targeting segment comprising a nucleotide sequence that is complementary to a target sequence in a target DNA molecule; and b) a protein-binding segment comprising two complementary stretches of nucleotides that hybridize to form a double-stranded RNA (dsRNA) duplex, wherein said two complementary stretches of nucleotides are covalently linked to one another with intervening nucleotides, and wherein said engineered guide ribonucleic acid polynucleotide is configured to form a complex with an endonuclease comprising a variant having at least 75% sequence identity to any one of SEQ ID NOs: 1-198, 221-459, 463-612, or 617-668. In some embodiments, said DNA-targeting segment is positioned 5' of both of said two complementary stretches of nucleotides. In some embodiments: a) said protein binding segment comprises a sequence having at least at least 70%, at least 80%, or at least 90% identical to any one of SEQ ID NOs:199-200 or 669-673; b) said protein binding segment comprises a sequence having at least 70%, at least 80%, or at least 90% identical to the nonvariable nucleotides of any one of SEQ ID NOs: 201-203 or 613-616. In some embodiments: a) said endonuclease comprises a sequence at least 70%, at least 80%, or at least 90% identical to any one of SEQ ID NOs: 2, 10, or 17; and b)

said guide RNA structure comprises a sequence at least 70%, at least 80%, or at least 90% identical to at least one of SEQ ID NO: 200 or the nonvariable nucleotides of SEQ ID NO: 202-203 or 613-614. In some embodiments: a) said endonuclease comprises a sequence at least 70%, at least 80%, or at least 90% identical to any one of SEQ ID NOs: 25-198, 221-459, or 489-580; and b)

said guide RNA structure comprises a sequence at least 70%, at least 80%, or at least 90% identical to a class 2, type II sgRNA. In some embodiments, said endonuclease further comprises a base editor or a histone editor coupled to said endonuclease. In some embodiments, said base editor is an adenosine deaminase. In some embodiments, said adenosine deaminase comprises ADAR1 or ADAR2. In some embodiments, said base editor is a cytosine deaminase. In some embodiments, said cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

In some aspects, the present disclosure provides for a deoxyribonucleic acid polynucleotide encoding any of the engineered guide ribonucleic acid polynucleotides described herein.

In some aspects, the present disclosure provides for a nucleic acid comprising an engineered nucleic acid sequence optimized for expression in an organism, wherein said nucleic acid encodes a class 2, type II Cas endonuclease comprising a RuvC domain and an HNH domain, wherein said endonuclease is derived from an uncultivated microorganism, and wherein said endonuclease has a molecular weight of about 120 kDa or less, 100 kDa or less, 90 kDa or less, 60 kDa or less, or 30 kDa or less. In some embodiments, said endonuclease comprises SEQ ID NOs: 1-198, 221-459, 463-612, or 617-668 or a variant thereof having at least 70% sequence identity thereto. In some embodiments, said endonuclease further comprises a sequence encoding one or more nuclear localization sequences (NLSs) proximal to an N- or C-terminus of said endonuclease. In some embodiments, said NLS comprises a sequence selected from SEQ ID NOs: 205-220. In some embodiments, said organism is prokaryotic, bacterial, eukaryotic, fungal, plant, mammalian, rodent, or human. In some embodiments, said organism is prokaryotic or bacterial, and said organism is a different organism from an organism from which said endonuclease is derived. In some embodiments, said organism is not said uncultivated microorganism.

In some aspects, the present disclosure provides for a vector comprising a nucleic acid sequence encoding an RNA-guided endonuclease comprising a RuvC-I domain and an HNH domain, wherein said endonuclease is derived from an uncultivated microorganism, and wherein said endonuclease has a molecular weight of about 120 kDa or less, 100 kDa or less, 90 kDa or less, or 60 kDa or less, wherein the RNA-guided endonuclease is optionally archaeal. In some embodiments, said endonuclease further comprises an arginine-rich region comprising an RRxRR motif or a domain with PF14239 homology. In some embodiments, said endonuclease further comprises a REC (recognition) domain. In some embodiments, said endonuclease further comprises a BH domain, a WED domain, and a PI domain.

In some aspects, the present disclosure provides for a vector comprising any of the nucleic acids described herein. In some embodiments, the vector further comprising a nucleic acid encoding an engineered guide ribonucleic acid structure configured to form a complex with said endonuclease, said engineered guide ribonucleic acid structure comprising: a) a guide ribonucleic acid sequence configured to hybridize to a target deoxyribonucleic acid sequence; and b) a tracr ribonucleic acid sequence configured to binding to said endonuclease. In some embodiments, the vector is a plasmid, a minicircle, a CELiD, an adeno-associated virus (AAV) derived virion, or a lentivirus.

In some aspects, the present disclosure provides for a cell comprising any of the vectors described herein. In some embodiments, said cell is a bacterial, archaeal, fungal, eukaryotic, mammalian, or plant cell. In some embodiments, said cell is a bacterial cell.

In some aspects, the present disclosure provides for a method of manufacturing an endonuclease, comprising cultivating any of the cells described herein.

In some aspects, the present disclosure provides for a method for binding, cleaving, marking, or modifying a double-stranded deoxyribonucleic acid polynucleotide, comprising: (a) contacting said double-stranded deoxyribonucleic acid polynucleotide with a class 2, type II Cas endonuclease in complex with an engineered guide ribonucleic acid structure configured to bind to said endonuclease and said double-stranded deoxyribonucleic acid polynucleotide; (b) wherein said double-stranded deoxyribonucleic acid polynucleotide comprises a protospacer adjacent motif (PAM); wherein said endonuclease has a molecular weight of about 120 kDa or less, 100 kDa or less, 90 kDa or less, or 60 kDa or less. In some embodiments, said endonuclease cleaves said double-stranded deoxyribonucleic acid polynucleotide, wherein said PAM comprises NGG. In some embodiments, said endonuclease cleaves said double-stranded deoxyribonucleic acid polynucleotide 6-8 nucleotides or 7 nucleotides from said PAM. In some embodiments, said endonuclease comprises a variant with at least 70%, at least 75%, at least 80% or at least 90% sequence identity to any one of SEQ ID NOs: 1-198, 221-459, 463-612, or 617-668.

In some aspects, the present disclosure provides for a method for binding, cleaving, marking, or modifying a double-stranded deoxyribonucleic acid polynucleotide, comprising: (a) contacting said double-stranded deoxyribonucleic acid polynucleotide with an RNA-guided archaeal endonuclease in complex with an engineered guide ribonucleic acid structure configured to bind to said endonuclease and said double-stranded deoxyribonucleic acid polynucleotide; wherein said double-stranded deoxyribonucleic acid polynucleotide comprises a protospacer adjacent motif (PAM); and wherein said endonuclease comprises a variant with at least 70%, at least 75%, at least 80% or at least 90% sequence identity to any one of SEQ ID NOs: 1-198, 221-459, 463-612, or 617-668. In some embodiments, said endonuclease cleaves said double-stranded deoxyribonucleic acid polynucleotide, wherein said PAM comprises NGG. In some embodiments, said endonuclease cleaves said double-stranded deoxyribonucleic acid polynucleotide 6-8 or 7 nucleotides from said PAM. In some embodiments, said class 2, type II Cas endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said class 2, type II Cas endonuclease is derived from an uncultivated microorganism. In some embodiments, said double-stranded deoxyribonucleic acid polynucleotide is a prokaryotic, archaeal, bacterial, eukaryotic, plant, fungal, mammalian, rodent, or human double-stranded deoxyribonucleic acid polynucleotide. In some embodiments, said double-stranded deoxyribonucleic acid polynucleotide is a prokaryotic, archaeal, or bacterial double-stranded deoxyribonucleic acid polynucleotide from a species other than a species from which said endonuclease was derived.

In some aspects, the present disclosure provides for a method of modifying a target nucleic acid locus, said method comprising delivering to said target nucleic acid locus any of the engineered nuclease systems described herein, wherein said endonuclease is configured to form a complex with said engineered guide ribonucleic acid structure, and wherein said complex is configured such that upon binding of said complex to said target nucleic acid locus, said complex modifies said target nucleic locus. In some embodiments, modifying said target nucleic acid locus comprises binding, nicking, cleaving, or marking said target nucleic acid locus. In some embodiments, said target nucleic acid locus comprises deoxyribonucleic acid (DNA) or ribonucleic acid (RNA). In some embodiments, said target nucleic acid comprises genomic eukaryotic DNA, archaeal DNA, viral DNA, or bacterial DNA. In some embodiments, said target nucleic acid comprises bacterial DNA wherein said bacterial DNA is derived from a bacterial or archaeal species different from a species from which said endonuclease was derived. In some embodiments, said target nucleic acid locus is in vitro. In some embodiments, said target nucleic acid locus is within a cell. In some embodiments, said endonuclease and said engineered guide nucleic acid structure are encoded by separate nucleic acid molecules. In some embodiments, said cell is a prokaryotic cell, a bacterial cell, an archaeal cell, a eukaryotic cell, a fungal cell, a plant cell, an animal cell, a mammalian cell, a rodent cell, a primate cell, or a human cell. In some embodiments, said cell is derived from a species different from a species from which said endonuclease was derived. In some embodiments, delivering said engineered nuclease system to said target nucleic acid locus comprises delivering any of the nucleic acids described herein or any of the vectors described herein. In some embodiments, delivering said engineered nuclease system to said target nucleic acid locus comprises delivering a nucleic acid comprising an open reading frame encoding said endonuclease. In some embodiments, said nucleic acid comprises a promoter to which said open reading frame encoding said endonuclease is operably linked. In some embodiments, delivering said engineered nuclease system to said target nucleic acid locus comprises delivering a capped mRNA containing said open reading frame encoding said endonuclease. In some embodiments, delivering said engineered nuclease system to said target nucleic acid locus comprises delivering a translated polypeptide. In some embodiments, delivering said engineered nuclease system to said target nucleic acid locus comprises delivering a deoxyribonucleic acid (DNA) encoding said engineered guide ribonucleic acid structure operably linked to a ribonucleic acid (RNA) pol III promoter. In some embodiments, said endonuclease induces a single-stranded break or a double-stranded break at or proximal to said target locus. In some embodiments, said endonuclease induces a double stranded break proximal to said target locus 5' from a protospacer adjacent motif (PAM). In some embodiments, said endonuclease induces a double-stranded break 6-8 nucleotides or 7 nucleotides 5' from said PAM. In some embodiments, said engineered nuclease system induces a chemical modification of a nucleotide base within or proximal to said target locus or a chemical modification of a histone within or proximal to said target locus. In some embodiments, said chemical modification is deamination of an adenosine or a cytosine nucleotide. In some embodiments, said endonuclease further comprises a base editor coupled to said endonuclease. In some embodiments, said base editor is an adenosine deaminase. In some embodiments, said adenosine deaminase comprises ADAR1 or ADAR2. In some embodiments, said base editor is a cytosine deaminase. In some embodiments, said cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A shows a SMART phylogenetic tree in context of Cas9 reference sequences, where SMART effectors are distantly clustered away from Cas9 reference sequences (Type II-A, II-B, and II-C); FIG. 1B shows a SMART phylogenetic tree illustrating subgroups of SMART enzymes.

(FIG. 3A) genomic context of the SMART I MG33-1 nuclease and CRISPR loci encoded upstream from a SMART II nuclease MG35-236, showing downstream from the SMART II a predicted insertion sequence carrying transposases TnpA and TnpB;: (FIG. 3B): genomic context of the SMART I nuclease MG34-1, where environmental expression sequencing reads are shown aligned under the CRISPR array and the predicted tracrRNA, and the transcriptomic coverage for the regions is illustrated above the contig sequence; (FIG. 3C) genomic context of the SMART I nuclease MG34-16, wherein environmental expression sequencing reads are shown aligned under the CRISPR array and the predicted tracrRNA, and the transcriptomic coverage for the regions is illustrated above the contig sequence; and (FIG. 3D) a genomic fragment targeted by spacer 7 from the MG34-16 CRISPR array in FIG. 3D, where the genomic fragment was identified as being derived from phage based on virus-specific gene annotations terminase and portal; the inset shows the location of the MG34-16 spacer 7 targeting the C-terminus of a viral gene of unknown function—the putative NGG PAM for MG34-16 is highlighted by a grey box downstream from the spacer match.

(FIG. 4A) an alignment of the endonuclease region containing the RuvC-I and bridge helix domains; (FIG. 4B) an alignment of the region containing the RuvC-III domain; and (FIG. 4C) an alignment of the region containing the RuvC-II and HNH domains (FIG. 5B) a multiple sequence alignment overview of two SMART I nucleases relative to reference Cas9 nuclease sequences, wherein RuvC and HNH catalytic residues are shown as black bars above each sequence, regions that align in 3D space with the crystal structure of SaCas are represented by rounded boxes, and dashed lines represent regions with poor or no alignment in 3D space between the 3D structure prediction of the SMART and SaCas9.

(FIG. 6B) a multiple sequence alignment overview of two SMART II nucleases relative to reference Cas9 nuclease sequences, where RuvC and HNH catalytic residues are shown as black bars above each sequence, regions that align in 3D space with the crystal structure of SaCas are represented by rounded boxes, and residues identified from 3D structure prediction which may be involved in recognizing a guide/target/PAM sequence are represented by dark grey boxes above the MG35-419 sequence (within the RRXRR and REC domains).

(FIG. 7B) a dot plot of length of individual SMART I domains of enzymes described herein.

(FIG. 8B) a histogram of count frequency of RRXRR motifs in various types of class 2 Cas enzymes. In FIGS. 8A-8B, lines track the mean count value, while outliers are represented by dots.

(FIG. 9B) MG34-1 sgRNA 2; (FIG. 9C) MG34-9 sgRNA 1, and (FIG. 9D) MG34-16 sgRNA 1.

FIG. 10A shows an Agilent TapeStation® gel of the ligation products of a cleavage assay for MG34-1 with two sgRNA designs vs. the negative control. Lane L3: ladder. Lane A4: Apo, no sgRNA. Lanes B4 and C4: MG34-1 sgRNAs tested (sg1: SEQ ID No. 612, sg2: 613). Cleavage product bands are labeled with arrows. Lanes G3 and H3: greyed out, not relevant to this experiment. FIG. 10B shows a PCR gel of the ligation products show activity of MG34-1, 34-9 and 34-16. Lane 1: ladder. Lanes 2-7: sgRNA designs with six spacer lengths for MG34-1. Lanes 8 and 9: sgRNA design for 34-9 and 34-16, respectively. Arrows indicate cleavage confirmation bands.

FIG. 11A shows a SeqLogo representation of a consensus PAM sequence (NGGN) for MG34-1 with sgRNA 1 (top, SEQ ID NO: 612) and sgRNA 2 (bottom, SEQ ID NO: 613). FIG. 11B shows a histogram showing the location of the cut site for MG34-1, demonstrating that MG34-1 prefers to cleave at about position 7 from the PAM. FIG. 11C shows a sanger sequencing chromatogram shows a preferred NGG PAM for MG34-9 (highlighted with a box). The arrow indicates the cut site at position 7 from the PAM.

FIGS. 12A-12B illustrate the results of plasmid targeting experiments in E. coli for MG 34-1. FIG. 12A shows replica plating of E. coli strains demonstrating plasmid cutting; E. coli expressing MG34-1 and a sgRNA were transformed with a kanamycin resistance plasmid containing a target for the sgRNA (+sp). Plate quadrants that show growth impairment (+sp) vs. the negative control (without the target and PAM (−sp)) indicate successful targeting and cleavage by the enzyme. The experiment was replicated twice and performed in triplicate. FIG. 12B shows graphs of colony forming unit (cfu) measurements from the replica plating experiments in A showing growth repression in the target condition (+sp) vs. the non-target control (−sp), demonstrating the plasmid was cut.

FIG. 13A shows the genomic context of the SMART II MG35-419 effector and CRISPR loci encoded in the vicinity. FIG. 13B shows the genomic context of the SMART II effector MG35-3 showing a transcribed 5' UTR.

BRIEF DESCRIPTION OF THE SEQUENCE LISTING

Figures 1A, 1B:
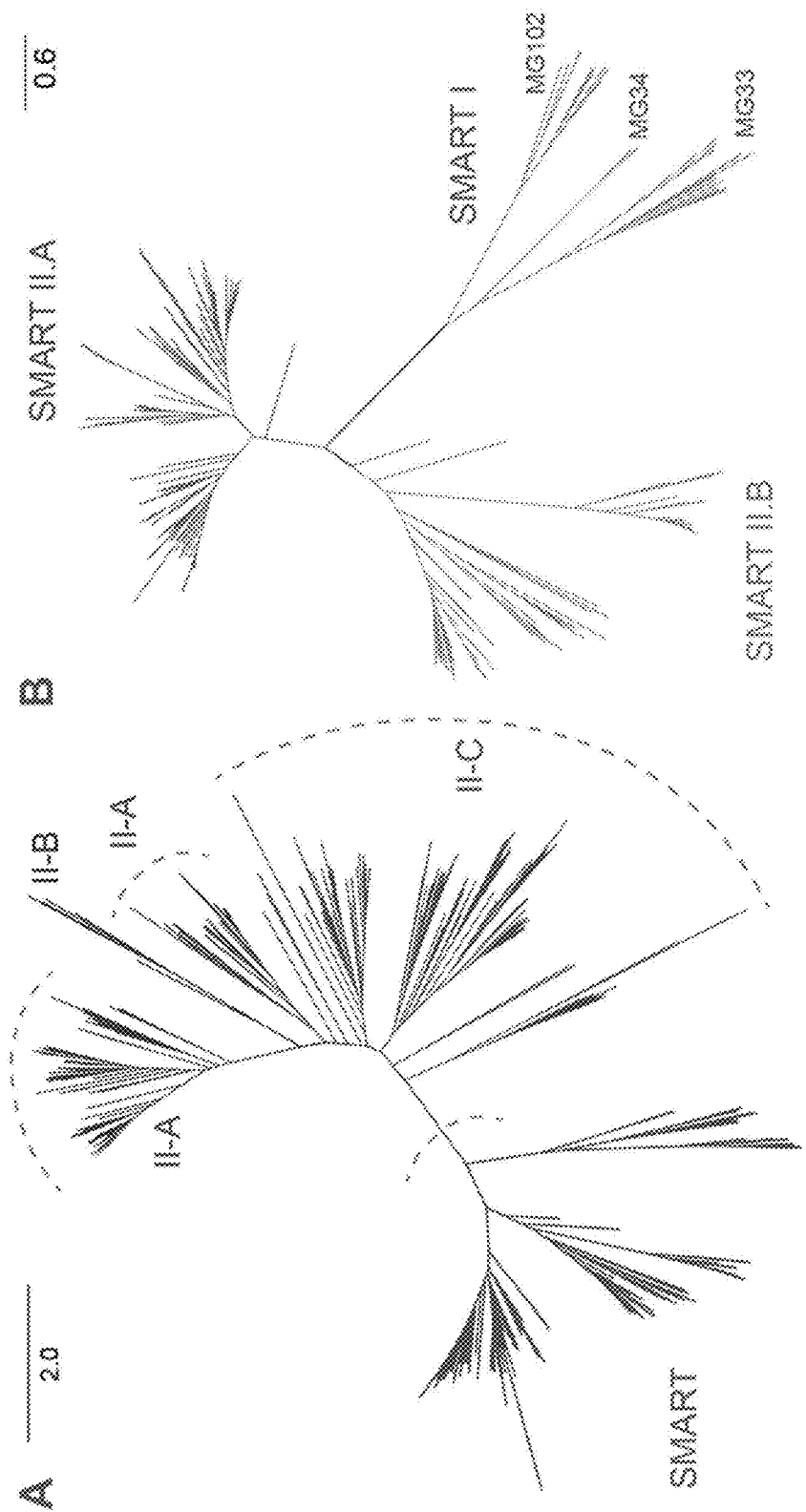
FIGS. 1A-1B depict a dendrogram showing homology relationships of CRISPR/Cas loci of different classes and types. Shown are SMART I and II Cas enzyme classes described herein relative to Class 2, Type II-A, II-B, and II-C Cas systems, demonstrating that these systems group into separate classes than II-A, II-B, and II-C.

The Sequence Listing filed herewith provides exemplary polynucleotide and polypeptide sequences for use in methods, compositions and systems according to the disclosure. Below are exemplary descriptions of sequences therein.

MG33 Nucleases

SEQ ID NOs: 1 and 463-486 shows the full-length peptide sequence of a MG33 nuclease.

SEQ ID NOs: 199 and 669-670 show the nucleotide sequence of a tracrRNA predicted to function with an MG33 nuclease.

SEQ ID NO: 201 shows the nucleotide sequence of a predicted single-guide RNA (sgRNA) sequence predicted to function with an MG33 nuclease. "N"s denote variable residues and non-N-residues represent the scaffold sequence.

MG34 Nucleases

SEQ ID NOs: 2-24 and 487-488 show the full-length peptide sequences of MG34 nucleases.

SEQ ID NO: 200 shows the nucleotide sequence of a tracrRNA predicted to function with an MG34 nuclease.

SEQ ID NOs: 202,203, and 613-616 show the nucleotide sequences of predicted single-guide RNA (sgRNA) sequences predicted to function with an MG34 nuclease. "N"s denote variable residues and non-N-residues represent the scaffold sequence.

MG35 Nucleases

SEQ ID NOs: 25-198,221-459, 489-580, and 617-668 show the full-length peptide sequences of MG35 nucleases.

SEQ ID NOs: 460-461 show the nucleotide sequences of MG35 tracrRNAs derived from the same loci as MG35 nucleases.

SEQ ID NO: 462 shows a repeat of MG35 nucleases described herein.

MG102 Nucleases

SEQ ID NOs: 581-612 show the full-length peptide sequences of MG102 nucleases.

SEQ ID NOs: 672-673 show the nucleotide sequences of MG102 tracrRNAs derived from the same loci as MG102 nucleases SEQ ID NOs: 205-220 show the sequences of example nuclear localization sequences (NLSs) that can be appended to nucleases according to the disclosure.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The practice of some methods disclosed herein employ, unless otherwise indicated, techniques of immunology, biochemistry, chemistry, molecular biology, microbiology, cell biology, genomics and recombinant DNA. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)) (which is entirely incorporated by reference herein).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

As used herein, a "cell" generally refers to a biological cell. A cell may be the basic structural, functional and/or biological unit of a living organism. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc., a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be synthetically made, sometimes termed an artificial cell).

The term "nucleotide," as used herein, generally refers to a base-sugar-phosphate combination. A nucleotide may comprise a synthetic nucleotide. A nucleotide may comprise a synthetic nucleotide analog. Nucleotides may be monomeric units of a nucleic acid sequence (e.g., deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives may include, for example, [aS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled, such as using moieties comprising optically detectable moieties (e.g., fluorophores). Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-λ-rhodamine (ROX), 4-(4'dimethylaminophenylazo) benzoic acid (DABCYL), Cascade Blue®, Oregon Green®, Texas Red®, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G] ddATP, [dR110]ddCTP, [dTAMRA]ddGTP, and [dROX] ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY™-FL-14-UTP, BODIPY™-FL-4-UTP, BODIPY™-TMR-14-UTP, BODIPY™-TMR-14-dUTP, BODIPY™-TR-14-UTP, BODIPY™-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP). .A nucleotide may comprise a nucleotide analog. In some embodiments, nucleotide analogs may comprise structures of natural nucleotides that are modified at any position so as to alter certain chemical properties of the nucleotide yet retain the ability of the nucleotide analog to perform its intended function (e.g. hybridization to other nucleotides in RNA or DNA). Examples of positions of the nucleotide which may be derivatized include the 5 position, e.g., 5-(2-amino) propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine: O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310. Nucleotide analogs may also comprise modifications to the sugar portion of the nucleotides. For example the 2' OH-group may be replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine: O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310. Nucleotide analogs may also comprise modifications to the sugar portion of the nucleotides. For example the 2' OH-group may be replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The terms "polynucleotide," "oligonucleotide," and "nucleic acid" are used interchangeably to generally refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure and may perform any function. A polynucleotide may comprise one or more analogs (e.g., altered backbone, sugar, or nucleobase). If present, modifications to the nucleotide structure may be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

The terms "transfection" or "transfected" generally refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88 (which is entirely incorporated by reference herein).

The terms "peptide," "polypeptide," and "protein" are used interchangeably herein to generally refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer may be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids may include natural amino acids and non-natural amino acids, which have been chemically modified to include a group or a chemical moiety not naturally present on the amino acid. Amino acid analogues may refer to amino acid derivatives. The term "amino acid" includes both D-amino acids and L-amino acids.

As used herein, the term "non-native" can generally refer to a nucleic acid or polypeptide sequence that is not found in a native nucleic acid or protein. Non-native may refer to affinity tags. Non-native may refer to fusions. Non-native may refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that may also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide.

The term "promoter", as used herein, generally refers to the regulatory DNA region which controls transcription or expression of a gene and which may be located adjacent to or overlapping a nucleotide or region of nucleotides at which RNA transcription is initiated. A promoter may contain specific DNA sequences which bind protein factors, often referred to as transcription factors, which facilitate binding of RNA polymerase to the DNA leading to gene transcription. A 'basal promoter', also referred to as a 'core promoter', may generally refer to a promoter that contains all the basic necessary elements to promote transcriptional expression of an operably linked polynucleotide. Eukaryotic basal promoters typically, though not necessarily, contain a TATA-box and/or a CAAT box.

The term "expression", as used herein, generally refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof generally refer to juxtaposition of genetic elements, e.g., a promoter, an enhancer, a polyadenylation sequence, etc., wherein the elements are in a relationship permitting them to operate in the expected manner. For instance, a regulatory element, which may comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein, generally refers to a macromolecule or association of macromolecules that comprises or associates with a polynucleotide and which may be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target.

As used herein, "an expression cassette" and "a nucleic acid cassette" are used interchangeably generally to refer to a combination of nucleic acid sequences or elements that are expressed together or are operably linked for expression. In some cases, an expression cassette refers to the combination of regulatory elements and a gene or genes to which they are operably linked for expression.

A "functional fragment" of a DNA or protein sequence generally refers to a fragment that retains a biological activity (either functional or structural) that is substantially similar to a biological activity of the full-length DNA or protein sequence. A biological activity of a DNA sequence may be its ability to influence expression in a manner known to be attributed to the full-length sequence.

As used herein, an "engineered" object generally indicates that the object has been modified by human intervention. According to non-limiting examples: a nucleic acid may be modified by changing its sequence to a sequence that does not occur in nature; a nucleic acid may be modified by ligating it to a nucleic acid that it does not associate with in nature such that the ligated product possesses a function not present in the original nucleic acid; an engineered nucleic acid may synthesized in vitro with a sequence that does not exist in nature; a protein may be modified by changing its amino acid sequence to a sequence that does not exist in nature; an engineered protein may acquire a new function or property. An "engineered" system comprises at least one engineered component.

As used herein, the term "optimally aligned" generally refers to an alignment of two amino acid sequences that give the highest percent identity score or maximizes the number of matched residues.

As used herein, "synthetic" and "artificial" are used interchangeably to refer to a protein or a domain thereof that has low sequence identity (e.g., less than 50% sequence identity, less than 25% sequence identity, less than 10% sequence identity, less than 5% sequence identity, less than 1% sequence identity) to a naturally occurring human protein. For example, VPR and VP64 domains are synthetic transactivation domains.

The term "tracrRNA" or "tracr sequence", as used herein, can generally refer to a nucleic acid with at least about 5%, 10%, 20%, 30%, 40%, 50%, 60%, 70%, 80%, 90%, 95%, or 100% sequence identity and/or sequence similarity to a wild type exemplary tracrRNA sequence (e.g., a tracrRNA from S. pyogenes S. aureus, etc. or SEQ ID NOs: 199-203). tracrRNA can refer to a nucleic acid with at most about 5%, 10%, 20%, 30%, 40%, 50%, 60%, 70%, 80%, 90%, or 100% sequence identity and/or sequence similarity to a wild type exemplary tracrRNA sequence (e.g., a tracrRNA from S. pyogenes S. aureus, etc). tracrRNA may refer to a modified form of a tracrRNA that can comprise a nucleotide change such as a deletion, insertion, or substitution, variant, mutation, or chimera. A tracrRNA may refer to a nucleic acid that can be at least about 60% identical to a wild type exemplary tracrRNA (e.g., a tracrRNA from S. pyogenes S. aureus, etc.) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from S. pyogenes S. aureus, etc.) sequence over a stretch of at least 6 contiguous nucleotides. Type II tracrRNA sequences can be predicted on a genome sequence by identifying regions with complementarity to part of the repeat sequence in an adjacent CRISPR array.

As used herein, a "guide nucleic acid" can generally refer to a nucleic acid that may hybridize to another nucleic acid. A guide nucleic acid may be RNA. A guide nucleic acid may be DNA. The guide nucleic acid may be programmed to bind to a sequence of nucleic acid site-specifically. The nucleic acid to be targeted, or the target nucleic acid, may comprise nucleotides. The guide nucleic acid may comprise nucleotides. A portion of the target nucleic acid may be complementary to a portion of the guide nucleic acid. The strand of a double-stranded target polynucleotide that is complementary to and hybridizes with the guide nucleic acid may be called the complementary strand. The strand of the double-stranded target polynucleotide that is complementary to the complementary strand, and therefore may not be complementary to the guide nucleic acid may be called noncomplementary strand. A guide nucleic acid may comprise a polynucleotide chain and can be called a "single guide nucleic acid." A guide nucleic acid may comprise two polynucleotide chains and may be called a "double guide nucleic acid." If not otherwise specified, the term "guide nucleic acid" may be inclusive, referring to both single guide nucleic acids and double guide nucleic acids. A guide nucleic acid may comprise a segment that can be referred to as a "nucleic acid-targeting segment" or a "nucleic acid-targeting sequence." A nucleic acid-targeting segment may comprise a sub-segment that may be referred to as a "protein binding segment" or "protein binding sequence" or "Cas protein binding segment".

The term "sequence identity" or "percent identity" in the context of two or more nucleic acids or polypeptide sequences, generally refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation (E) of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at blast.ncbi.nlm.nih.gov); or CLUSTALW with parameters of the Smith-Waterman homology search algorithm with parameters of a match of 2, a mismatch of −1, and a gap of −1; MUSCLE with default parameters; MAFFT with parameters retree of 2 and maxiterations of 1000; Novafold with default parameters; HMMER hmmalign with default parameters.

As used herein, the term "RuvC III domain" generally refers to a third discontinuous segment of a RuvC endonuclease domain (the RuvC nuclease domain being comprised of three discontiguous segments, RuvC I, RuvC II, and RuvC III). A RuvC domain or segments thereof (e.g. RuvC I, RuvC II, or RuvC III) can generally be identified by alignment to known domain sequences, structural alignment to proteins with annotated domains, or by comparison to Hidden Markov Models (HMIs) built based on known domain sequences (e.g., Pfam HMM PF18541 for RuvC_III).

As used herein, the term "HNH domain" generally refers to an endonuclease domain having characteristic histidine and asparagine residues. An HNH domain can generally be identified by alignment to known domain sequences, structural alignment to proteins with annotated domains, or by comparison to Hidden Markov Models (HMMs) built based on known domain sequences (e.g., Pfam HMM PF01844 for domain HNH).

As used herein, the term "bridge helix domain" or "BH domain" generally refers to an arginine-rich helix domain present in Cas enzymes that plays an important role in initiating cleavage activity upon binding of target DNA.

As used herein, the term "recognition domain" or "REC domain" generally refers to a domain thought to interact with the repeat:anti-repeat duplex of the gRNA and to mediate the formation of a Cas endonuclease/gRNA complex.

As used herein, the term "wedge domain" or "WED domain" generally refers to a fold comprising a twisted five-stranded beta sheet flanked by four alpha helices, which is generally responsible for the recognition of the distorted repeat: anti-repeat duplex for Cas enzymes. WED domains can be responsible for the recognition of single-guide RNA scaffolds.

As used herein, the term "PAM interacting domain" or "PI domain" generally refers to a domain found in Cas enzymes positioned in the endonuclease-DNA-complex to recognize the PAM sequence on the non-complementary DNA strand of the guide RNA.

Overview

The discovery of new Cas enzymes with unique functionality and structure may offer the potential to further disrupt deoxyribonucleic acid (DNA) editing technologies, improving speed, specificity, functionality, and ease of use. Relative to the predicted prevalence of Clustered Regularly Interspaced Short Palindromic Repeats (CRISPR) systems in microbes and the sheer diversity of microbial species, relatively few functionally characterized CRISPR/Cas enzymes exist in the literature. This is partly because a huge number of microbial species may not be readily cultivated in laboratory conditions. Metagenomic sequencing from natural environmental niches that represent large numbers of microbial species may offer the potential to drastically increase the number of new CRISPR/Cas systems known and speed the discovery of new oligonucleotide editing functionalities. A recent example of the fruitfulness of such an approach is demonstrated by the 2016 discovery of CasX/CasY CRISPR systems from metagenomic analysis of natural microbial communities.

CRISPR/Cas systems are RNA-directed nuclease complexes that have been described to function as an adaptive immune system in microbes. In their natural context, CRISPR/Cas systems occur in CRISPR (clustered regularly interspaced short palindromic repeats) operons or loci, which generally comprise two parts: (i) an array of short repetitive sequences (30-40 bp) separated by equally short spacer sequences, which encode the RNA-based targeting element; and (ii) ORFs encoding the Cas encoding the nuclease polypeptide directed by the RNA-based targeting element alongside accessory proteins/enzymes. Efficient nuclease targeting of a particular target nucleic acid sequence generally requires both (i) complementary hybridization between the first 6-8 nucleic acids of the target (the target seed) and the crRNA guide; and (ii) the presence of a protospacer-adjacent motif (PAM) sequence within a defined vicinity of the target seed (the PAM usually being a sequence not commonly represented within the host genome). Depending on the exact function and organization of the system, CRISPR-Cas systems are commonly organized into 2 classes, 5 types and 16 subtypes based on shared functional characteristics and evolutionary similarity.

Class I CRISPR-Cas systems have large, multisubunit effector complexes, and comprise Types I, III, and IV.

Type I CRISPR-Cas systems are considered of moderate complexity in terms of components. In Type I CRISPR-Cas systems, the array of RNA-targeting elements is transcribed as a long precursor crRNA (pre-crRNA) that is processed at repeat elements to liberate short, mature crRNAs that direct the nuclease complex to nucleic acid targets when they are followed by a suitable short consensus sequence called a protospacer-adjacent motif (PAM). This processing occurs via an endoribonuclease subunit (Cash) of a large endonuclease complex called Cascade, which also comprises a nuclease (Cas3) protein component of the crRNA-directed nuclease complex. Cas I nucleases function primarily as DNA nucleases.

Type III CRISPR systems may be characterized by the presence of a central nuclease, known as Cas10, alongside a repeat-associated mysterious protein (RAMP) that comprises Csm or Cmr protein subunits. Like in Type I systems, the mature crRNA is processed from a pre-crRNA using a Cash-like enzyme. Unlike type I and II systems, type III systems appear to target and cleave DNA-RNA duplexes (such as DNA strands being used as templates for an RNA polymerase).

Type IV CRISPR-Cas systems possess an effector complex that consists of a highly reduced large subunit nuclease (csf1), two genes for RAMP proteins of the Cas5 (csf3) and Cas? (csf2) groups, and, in some cases, a gene for a predicted small subunit; such systems are commonly found on endogenous plasmids.

Class II CRISPR-Cas systems generally have single-polypeptide multidomain nuclease effectors, and comprise Types II, V and VI.

Type II CRISPR-Cas systems are considered the simplest in terms of components. In Type II CRISPR-Cas systems, the processing of the CRISPR array into mature crRNAs does not require the presence of a special endonuclease subunit, but rather a small trans-encoded crRNA (tracrRNA) with a region complementary to the array repeat sequence; the tracrRNA interacts with both its corresponding effector nuclease (e.g. Cas9) and the repeat sequence to form a precursor dsRNA structure, which is cleaved by endogenous RNAse III to generate a mature effector enzyme loaded with both tracrRNA and crRNA. Cas II nucleases are known as DNA nucleases. Type II effectors generally exhibit a structure consisting of a RuvC-like endonuclease domain that adopts the RNase H fold with an unrelated HNH nuclease domain inserted within the folds of the RuvC-like nuclease domain. The RuvC-like domain is responsible for the cleavage of the target (e.g., crRNA complementary) DNA strand, while the HNH domain is responsible for cleavage of the displaced DNA strand.

Type V CRISPR-Cas systems are characterized by a nuclease effector (e.g. Cas12) structure similar to that of Type II effectors, comprising a RuvC-like domain. Similar to Type II, most (but not all) Type V CRISPR systems use a tracrRNA to process pre-crRNAs into mature crRNAs; however, unlike Type II systems which requires RNAse III to cleave the pre-crRNA into multiple crRNAs, type V systems are capable of using the effector nuclease itself to cleave pre-crRNAs. Like Type-II CRISPR-Cas systems, Type V CRISPR-Cas systems are again known as DNA nucleases. Unlike Type II CRISPR-Cas systems, some Type V enzymes (e.g., Cas12a) appear to have a robust single-stranded nonspecific deoxyribonuclease activity that is activated by the first crRNA directed cleavage of a double-stranded target sequence.

Type VI CRISPR-Cas systems have RNA-guided RNA endonucleases. Instead of RuvC-like domains, the single polypeptide effector of Type VI systems (e.g. Cas13) comprises two HEPN ribonuclease domains. Differing from both Type II and V systems, Type VI systems also appear to not need a tracrRNA for processing of pre-crRNA into crRNA.

Similar to type V systems, however, some Type VI systems (e.g., C2C2) appear to possess robust single-stranded non-specific nuclease (ribonuclease) activity activated by the first crRNA directed cleavage of a target RNA.

Because of their simpler architecture, Class II CRISPR-Cas have been most widely adopted for engineering and development as designer nuclease/genome editing applications.

One of the early adaptations of such a system for in vitro use can be found in Jinek et al. (Science. 2012 Aug. 17; 337(6096):816-21, which is entirely incorporated herein by reference). The Jinek study first described a system that involved (i) recombinantly-expressed, purified full-length Cas9 (e.g., a Class II, Type II Cas enzyme) isolated from *S. pyogenes* SF370, (ii) purified mature ~42 nt crRNA bearing a ~20 nt 5' sequence complementary to the target DNA sequence desired to be cleaved followed by a 3' tracr-binding sequence (the whole crRNA being in vitro transcribed from a synthetic DNA template carrying a T7 promoter sequence); (iii) purified tracrRNA in vitro transcribed from a synthetic DNA template carrying a T7 promoter sequence, and (iv) Mg'. Jinek later described an improved, engineered system wherein the crRNA of (ii) is joined to the 5' end of (iii) by a linker (e.g., GAAA) to form a single fused synthetic guide RNA (sgRNA) capable of directing Cas9 to a target by itself (compare top and bottom panel of FIG. 2).

*Mali* et al. (Science. 2013 Feb. 15; 339(6121): 823-826.), which is entirely incorporated herein by reference, later adapted this system for use in mammalian cells by providing DNA vectors encoding (i) an ORF encoding codon-optimized Cas9 (e.g., a Class II, Type II Cas enzyme) under a suitable mammalian promoter with a C-terminal nuclear localization sequence (e.g., SV40 NLS) and a suitable polyadenylation signal (e.g., TK pA signal); and (ii) an ORF encoding an sgRNA (having a 5' sequence beginning with G followed by 20 nt of a complementary targeting nucleic acid sequence joined to a 3' tracr-binding sequence, a linker, and the tracrRNA sequence) under a suitable Polymerase III promoter (e.g., the U6 promoter).

MG Enzymes

In one aspect, the present disclosure provides for an engineered nuclease system. The engineered nuclease system may comprise (a) an endonuclease. In some cases, the endonuclease comprises a RuvC domain and an HNH domain. The endonuclease may be from an uncultivated microorganism. The endonuclease may be a Cas endonuclease. The endonuclease may be a class 2 endonuclease. The endonuclease may be a class 2, type II Cas endonuclease. The engineered nuclease system may comprise (b) an engineered guide ribonucleic acid structure. The engineered guide ribonucleic acid structure may be configured to form a complex with the endonuclease. In some cases, the engineered guide ribonucleic acid structure configured to form a complex with the endonuclease comprises a guide ribonucleic acid sequence. The guide ribonucleic acid sequence may be configured to hybridize to a target deoxyribonucleic acid sequence. In some cases, the engineered guide ribonucleic acid structure configured to form a complex with the endonuclease comprises a tracr ribonucleic acid sequence. The tracr ribonucleic acid sequence may be configured to bind to the endonuclease. In some cases, the endonuclease has a molecular weight of about 120 kDa or less, about 110 kDa or less, about 100 kDa or less, about 90 kDa or less, about 80 kDa or less, about 70 kDa or less, about 60 kDa or less, about 50 kDa or less, about 40 kDa or less, about 30 kDa or less, about 20 kDa or less, or about 10 kDa or less.

In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, or 617-668.

In one aspect, the present disclosure provides an engineered nuclease system. The engineered nuclease system may comprise (a) an endonuclease. The endonuclease may comprise a RuvC-1 domain or a RuvC domain. The endonuclease may comprise an HNH domain. The endonuclease may comprise a RuvC-1 domain and an HNH domain. The endonuclease may be a Cas endonuclease. The endonuclease may be a class 2 endonuclease. The endonuclease may be a class 2, type II Cas endonuclease. The engineered nuclease system may comprise (b) an engineered guide ribonucleic acid. The engineered guide ribonucleic acid structure may be configured to form a complex with the endonuclease. The guide ribonucleic acid structure configured to form a complex with the endonuclease may comprise a guide ribonucleic acid sequence. The guide ribonucleic acid sequence may be configured to hybridize to a target deoxyribonucleic acid sequence. The engineered guide ribonucleic acid structure configured to form a complex with the endonuclease may comprise a tracr ribonucleic acid sequence. The tracr ribonucleic acid sequence may be configured to bind to the endonuclease. The endonuclease may comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of 1-198, 221-459, 463-612, or 617-668. The endonuclease may be an archaeal endonuclease. The endonuclease may be a Class 2, Type II Cas endonuclease. The endonuclease may comprise an arginine rich region comprising an RRxRR motif or a domain with PF14239 homology. The arginine-rich region or domain with PF14239 homology can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an arginine rich region or a domain with PF14239 homology of any one of SEQ ID NOs: 1-198, 221-459, 463-612, or 617-668. The domain boundaries of the arginine rich domain or the domain with PF14239 homology can be identified by optimal alignment to MG34-1 or MG34-9. The endonuclease may comprise REC domain. The REC domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a REC domain of any one of SEQ ID NOs: 1-198, 221-459, 463-612, or 617-668. The domain boundaries of the REC domain can be identified by optimal alignment to MG34-1 or MG34-9. The endonuclease may comprise BH (Bridge Helix) domain. The BH domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a BH domain of any one of SEQ ID NOs: 1-198, 221-459, 463-612, or 617-668. The domain boundaries of the BH domain can be identified by optimal alignment to MG34-1 or MG34-9.

The endonuclease may comprise WED (wedge) domain. The WED domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a WED domain of any one of SEQ ID NOs: 1-198, 221-459, 463-612, or 617-668. The domain boundaries of the WED domain can be identified by optimal alignment to MG34-1 or MG34-9. The endonuclease may comprise PI (PAM interacting) domain. The PI domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a PI domain of any one of SEQ ID NOs: 1-198, 221-459, 463-612, or 617-668. The domain boundaries of the PI domain can be identified by optimal alignment to MG34-1 or MG34-9.

In some cases, the endonuclease is derived from an uncultivated microorganism. In some cases, the tracr ribonucleic acid sequence comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides from any one of SEQ ID NOs: 199-200, 460-461, or 669-673 or a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides of the nonvariable nucleotides of any one of SEQ ID NOs: 201-203 or 613-616.

In some cases, the guide nucleic acid structure comprises SEQ ID NO: 201. In some cases, the guide nucleic acid structure comprises SEQ ID NO: 202. In some cases, the guide nucleic acid structure comprises SEQ ID NO: 203. In some cases, the guide nucleic acid structure comprises SEQ ID NO: 201-203. In some cases, the guide nucleic acid structure comprises SEQ ID NO: 613. In some cases, the guide nucleic acid structure comprises SEQ ID NO: 614. In some cases, the guide nucleic acid structure comprises SEQ ID NO: 615. In some cases, the guide nucleic acid structure comprises SEQ ID NO: 616.

In one aspect, the present disclosure provides an engineered nuclease system. The engineered nuclease system may comprise (a) an engineered guide ribonucleic acid structure. The engineered guide ribonucleic acid structure may comprise a guide ribonucleic acid sequence. The guide ribonucleic acid sequence may be configured to hybridize to a target deoxyribonucleic acid sequence. The engineered guide ribonucleic acid structure may comprise a tracr ribonucleic acid sequence. The tracr ribonucleic acid sequence may be configured to bind to an endonuclease. In some cases, the tracr ribonucleic acid sequence comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides from any one of SEQ ID NOs: 199-200, 460-461, or 669-673 or a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 15, at least 20, at least 25, at least 30, at least 35, at least 40, at least 45, at least 50, at least 60, at least 70, at least 80 consecutive nucleotides of the nonvariable nucleotides of any one of SEQ ID NOs: 201-203 or 613-616.

In some cases, the engineered nuclease system comprises an endonuclease. The endonuclease may be a class 2 endonuclease. The endonuclease may be a Cas endonuclease. The endonuclease may be a class 2, Type II Cas endonuclease.

In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues. In some cases, the engineered guide ribonucleic acid structure comprises a single ribonucleic acid polynucleotide. The single ribonucleic acid polynucleotide may comprise the guide ribonucleic acid sequence and the tracr ribonucleic acid sequence.

In some cases, the guide ribonucleic acid sequence is complementary to a prokaryotic, bacterial, archaeal, eukaryotic, fungal, plant, mammalian, or human genomic sequence. In some cases, the guide ribonucleic acid sequence is complementary to a prokaryotic genomic sequence. In some cases, the guide ribonucleic acid sequence is complementary to a bacterial genomic sequence. In some cases, the guide ribonucleic acid sequence is complementary to an archaeal genomic sequence. In some cases, the guide ribonucleic acid sequence is complementary to a eukaryotic genomic sequence. In some cases, the guide ribonucleic acid sequence is complementary to a fungal genomic sequence. In some cases, the guide ribonucleic acid sequence is complementary to a plant genomic sequence. In some cases, the guide ribonucleic acid sequence is complementary to a mammalian genomic sequence. In some cases, the guide ribonucleic acid sequence is complementary to a human genomic sequence.

In some cases, the guide ribonucleic acid targeting sequence or spacer is 10-30 nucleotides in length, or 12-28 nucleotides in length, or 15-24 nucleotides in length. In some cases, the endonuclease comprises one or more nuclear localization sequences (NLSs) proximal to an N- or C-terminus of the endonuclease. In some cases, the NLS comprises a sequence selected from SEQ ID NOs: 205-220.

TABLE 1

Examples NLS Sequences that may be used with Cas effectors according to the present disclosure.

| Source | NLS amino acid sequence | SEQ ID NO: |
|---|---|---|
| SV40 NLS | PKKKRKV | 205 |
| nucleoplasmin bipartite | KRPAATKKAGQAKKKK | 206 |
| c-myc | PAAKRVKLD | 207 |
| c-myc | RQRRNELKRSP | 208 |
| hnRNPA1 M9 | NQSSNFGPMKGGNFGGRSSG PYGGGGQYFAKPRNQGGY | 209 |
| Importin-alpha IBB domain | RMRIZFKNKGKDTAELRRRR VEVSVELRKAKKDEQILKRRNV | 210 |
| Myoma T protein | VSRKRPRP | 211 |
| Myoma T protein | PPKKARED | 212 |
| p53 | PQPKKKPL | 213 |
| mouse c-abl IV | SALIKKKKKMAP | 214 |
| influenza virus NS1 | DRLRR | 215 |
| influenza virus NS1 | PKQKKRK | 216 |
| Hepatitis virus delta antigen | RKLKKKIKKL | 217 |
| mouse Mx1 protein | REKKKFLKRR | 218 |
| human poly (ADP-ribose) polymerase | KRKGDEVDGVDEVAKKKSKK | 219 |
| steroid hormone receptors glucocorticoid | RKCLQAGMNLEARKTKK | 220 |

Included in the current disclosure are variants of any of the enzymes described herein with one or more conservative amino acid substitutions. Such conservative substitutions can be made in the amino acid sequence of a polypeptide without disrupting the three-dimensional structure or function of the polypeptide. Conservative substitutions can be accomplished by substituting amino acids with similar hydrophobicity, polarity, and R chain length for one another. Additionally, or alternatively, by comparing aligned sequences of homologous proteins from different species, conservative substitutions can be identified by locating amino acid residues that have been mutated between species (e.g., non-conserved residues) without altering the basic functions of the encoded proteins. Such conservatively substituted variants may include variants with at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity to any one of the endonuclease protein sequences described herein. In some embodiments, such conservatively substituted variants are functional variants. Such functional variants can encompass sequences with substitutions such that the activity of one or more critical active site residues or guide RNA binding residues of the endonuclease are not disrupted. In some embodiments, a functional variant of any of the proteins described herein lacks substitution of at least one of the conserved or functional residues called out in FIG. 4. In some embodiments, a functional variant of any of the proteins described herein lacks substitution of all of the conserved or functional residues called out in FIG. 4. Also provided for by the disclosure herein are altered activity variants of any of the nucleases described herein. Such altered activity variants may comprise an inactivating mutation in one or more catalytic residues identified herein (e.g. in FIG. 4) or generally described for RuvC domains. Such altered activity variants may comprise a change-switch mutation in a catalytic residue of a RuvCI, RuvCII, or RuvCIII domain.

Conservative substitution tables providing functionally similar amino acids are available from a variety of references (see, for e.g., Creighton, Proteins: Structures and Molecular Properties (W H Freeman & Co.; 2nd edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Included in the current disclosure are variants of any of the endonucleases described herein with sequence identity to particular domains. The domain can be an arginine rich domain (e.g. a domain with PF14239 homology), a REC (recognition) domain, a BH (bridge helix) domain, a WED (wedge) domain, a PI (PAM-interacting) domain, a PF14239 homology domain, or any other domain described herein. In some embodiments, residues encompassing one or more of these domains is identified in a protein by alignment to one of the proteins below (e.g. when one of the proteins below and the protein of interest are optimally aligned), wherein the residue boundaries for example domains are described.

TABLE 2

Example domain boundaries for endonucleases described herein

| | RuvC-I | BH | REC | Domain w/ PF14239 homology | RuvC-II | HNH | RuvC-III | WED and PI |
|---|---|---|---|---|---|---|---|---|
| MG34-1 effector | 1-41 | 42-76 | 77-281 | 4-65; 123-339 | 282-323 | 324-459 | 460-551 | 552-747 |
| MG34-9 effector | 1-41 | 42-76 | 77-280 | 4-65; 123-338 | 281-322 | 323-490 | 491-582 | 583-778 |

In some cases, the engineered nuclease system further comprises a single-stranded DNA repair template. In some cases, the engineered nuclease system further comprises a double-stranded DNA repair template. In some cases, the single- or double-stranded DNA repair template comprises from 5' to 3' a first homology arm comprising a sequence of at least 20 nucleotides 5' to the target deoxyribonucleic acid sequence. In some cases, the single- or double-stranded DNA repair template comprises from 5' to 3' a synthetic DNA sequence of at least 10 nucleotides. In some cases, the single- or double-stranded DNA repair template comprises from 5' to 3' a second homology arm comprising a sequence of at least 20 nucleotides 3' to the target sequence. In some cases, the single- or double-stranded DNA repair template comprises from 5' to 3': a first homology arm comprising a sequence of at least 20 nucleotides 5' to the target deoxyribonucleic acid sequence, a synthetic DNA sequence of at least 10 nucleotides, or a second homology arm comprising a sequence of at least 20 nucleotides 3' to the target sequence.

In some cases, the first homology arm comprises a sequence of at least 10, at least 20, at least 30, at least 40, at least 50, at least 60, at least 70, at least 80, at least 90, at least 100, at least 110, at least 120, at least 130, at least 140, at least 150, at least 175, at least 200, at least 250, at least 300, at least 400, at least 500, at least 750, or at least 1000 nucleotides. In some cases, the engineered nuclease system further comprises a source of Mg 2+. In some cases, the endonuclease and the tracr ribonucleic acid sequence are derived from distinct bacterial species. In some cases, the endonuclease and the tract ribonucleic acid sequence are derived from distinct bacterial species within a same phylum.

In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-24 or 462-488. In some cases, the guide RNA structure comprises an RNA sequence predicted to comprise a hairpin. In some cases, the hair pin comprises a stem and a loop. In some cases, the stem comprises at least 12 pairs, at least 14 pairs, at least 16 pairs or at least 18 pairs or ribonucleotides.

In some cases, the guide RNA structure further comprises a second stem and a second loop. In some cases, the second step comprises at least 5 pairs, at least 6 pairs, at least 7 pairs, at least 8 pairs, at least 9 pairs or at least 10 pairs of ribonucleotides. In some cases, the guide RNA structure further comprises an RNA structure and this RNA structure comprises at least two hairpins. In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 1 and the guide RNA structure comprises an RNA sequence predicted to comprise at least four hairpins. In some cases, each of these four hairpins comprises a stem and a loop.

In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some cases, the engineered nuclease system comprises the guide RNA structure which comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to at least one of SEQ ID NO: 199 or the nonvariable nucleotides of SEQ ID NO: 201.

In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 1-24 or 462-488. In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 199-200 or 669-673 or the nonvariable nucleotides of any one of SEQ ID NOs: 201-203 or 613-616.

In some cases, the sequence identity is determined by a BLASTP, CLUSTALW, MUSCLE, MAFFT, or CLUSTALW with the Smith-Waterman homology search algorithm parameters. In some cases, the sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some cases, the endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some cases, the endonuclease has less than less than 80% identity, less than 75% identity, less than 70% identity, less than 65% identity, less than 60% identity, less than 55% identity, or less than 50% identity to a Cas9 endonuclease.

In one aspect, the present disclosure provides an engineered guide RNA comprising (a) a DNA-targeting segment. In some cases, the DNA-targeting segment comprises a nucleotide sequence that is complementary to a target sequence in a target DNA molecule. In some cases, the engineered single guide ribonucleic acid polynucleotide comprises a protein-binding segment. The protein-binding segment comprises two complementary stretches of nucleotides that hybridize to form a double-stranded RNA (dsRNA) duplex. In some cases, the two complementary stretches of nucleotides are covalently linked to one another with intervening nucleotides. In some cases, the engineered guide ribonucleic acid polynucleotide is configured to form a complex with an endonuclease comprising a variant having at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, or 617-668.

In some cases, the DNA-targeting segment is positioned 5' of both of the two complementary stretches of nucleotides. In some cases, the protein binding segment comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 199-200 or 669-673 or the nonvariable nucleotides of any one of SEQ ID NOs: 201-203 or 613-616. In some cases, a deoxyribonucleic acid polynucleotide encodes the engineered guide ribonucleic acid polynucleotide described herein.

In one aspect, the present disclosure provides a nucleic acid comprising an engineered nucleic acid sequence. In some cases, the engineered nucleic acid sequence is optimized for expression in an organism. In some cases, the nucleic acid encodes an endonuclease. The endonuclease may be a Cas endonuclease. The endonuclease may be a class 2 endonuclease. The endonuclease may be a class 2, type II Cas endonuclease. In some cases, the endonuclease comprises a RuvC domain and an HNH domain. In some cases, the endonuclease is derived from an uncultivated microorganism. In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues. In some cases, the endonuclease comprises SEQ ID NOs: 1-198, 221-459, 463-612, or 617-668 or a variant thereof having at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto. In some cases, the endonuclease further comprises a sequence encoding one or more nuclear localization sequences (NLSs) proximal to an N- or C-terminus of said endonuclease. In some cases, the NLS comprises a sequence selected from SEQ ID NOs: 205-220.

In some cases, the organism is prokaryotic, bacterial, eukaryotic, fungal, plant, mammalian, rodent, or human. In some cases, the organism is prokaryotic. In some cases, the organism is bacterial. In some cases, the organism is eukaryotic. In some cases, the organism is fungal. In some cases, the organism is plant. In some cases, the organism is mammalian. In some cases, the organism is rodent. In some cases, the organism is human. Where the organism is prokaryotic or bacterial, then the organism may be a different organism from an organism from which the endonuclease is derived. In some cases, the organisms is not the uncultivated microorganism.

In one aspect, the present disclosure provides a vector which comprises a nucleic acid sequence. In some cases, the nucleic acid sequence encodes an endonuclease. In some cases, the endonuclease is a Cas endonuclease. In some cases, the endonuclease is a class 2 endonuclease. In some cases, the endonuclease is a class 2, type II Case endonuclease. The endonuclease may comprise a RuvC-I domain and an HNH domain. In some cases, the endonuclease is derived from an uncultivated microorganism. In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues.

In some aspects, the present disclosure provides for an endonuclease described herein configured to induce a double stranded break proximal to said target locus 5' to a protospacer adjacent motif (PAM). The endonuclease can induce a double-stranded break 6-8 nucleotides from the PAM or 7 nucleotides from the PAM. In some aspects, the present disclosure provides for an endonuclease described herein configured to induce a single-stranded break proximal to said target locus 5' to a protospacer adjacent motif (PAM). The endonuclease can induce a single-stranded break 6-8 nucleotides from the PAM or 7 nucleotides from the PAM. In some cases, an endonuclease configured to induce a single-stranded break comprises an inactivating mutation in one or more catalytic residues of an endonuclease described herein.

In some aspects, the present disclosure provides for an endonuclease system described herein configured to cause a chemical modification of a nucleotide base within or proximal to a target locus targeted by the endonuclease system. In this case, chemical modification of a nucleotide base generally refers to modification of the chemical moiety involved in base-pairing rather than modification of the sugar or phosphate portion of the nucleotide. The chemical modification can comprise deamination of an adenosine or a cytosine nucleotide. In some cases, endonuclease systems configured to cause a chemical modification comprises an endonuclease having a base editor coupled or fused in frame to said endonuclease. The endonuclease to which the base editor is fused or coupled can comprise a deactivating mutation in at least one catalytic residue of the endonuclease (e.g. in the RuvC domain). The base editor can be fused N- or C-terminally to said endonuclease, or linked via chemical conjugation. Base editors can include any adenosine or cytosine deaminases, including but not limited to Adenosine Deaminase RNA Specific 1 (ADAR1), Adenosine Deaminase RNA Specific 2 (ADAR2), Apolipoprotein B MRNA Editing Enzyme Catalytic Subunit 1 (APOBEC1), Apolipoprotein B MRNA Editing Enzyme Catalytic Subunit 2 (APOBEC2), Apolipoprotein B MRNA Editing Enzyme Catalytic Subunit 3A (APOBEC3A), Apolipoprotein B MRNA Editing Enzyme Catalytic Subunit 3B (APOBEC3B), Apolipoprotein B MRNA Editing Enzyme Catalytic Subunit 3C (APOBEC3C), Apolipoprotein B MRNA Editing Enzyme Catalytic Subunit 3D (APOBEC3D), Apolipoprotein B MRNA Editing Enzyme Catalytic Subunit 3F (APOBEC3F), Apolipoprotein B MRNA Editing Enzyme Catalytic Subunit 3G (APOBEC3G), Apolipoprotein B MRNA Editing Enzyme Catalytic Subunit 3H (APOBEC3H), or Apolipoprotein B MRNA Editing Enzyme Catalytic Subunit 4 (APOBEC4), or a functional fragment thereof. The base editor can comprise a yeast, eukaryotic, mammalian, or human base editor.

In some aspects, the present disclosure provides for an endonuclease system described herein configured to cause a chemical modification of histone within or proximal to a target locus targeted by the endonuclease system. In some cases, endonuclease systems configured to cause a chemical modification of a histone comprise an endonuclease having a histone editor coupled or fused in frame to said endonuclease. The histone editor can be coupled or fused N- or C-terminally to the endonuclease. In some embodiments, the chemical modification can comprise methylation, acetylation, demethylation, or deacetylation. The endonuclease to which the histone editor is fused or coupled can comprise a deactivating mutation in at least one catalytic residue of the endonuclease (e.g. in the RuvC domain). The histone editor can comprise a histone methyltransferase (e.g. ASH1L, DOT1L, EHMT1, EHMT2, EZH1, EZH2, MLL, MLL2, MLL3, MLL4, MLL5, NSD1, PRDM2, SET, SETBP1, SETD1A, SETD1B, SETD2, SETD3, SETD4, SETD5, SETD6, SETD7, SETD8, SETD9, SETDB1, SETDB2, SETMAR, SMYD1, SMYD2, SMYD3, SMYD4, SMYD5, SUV39H1, SUV39H2, SUV420H1, or SUV420H2), a histone demethylase (e.g. the KDM1, KDM2, KDM3, KDM4, KDM5, or KDM6 families), a histone acetyltransferase (e.g. GNATs or HAT family acetyltransferases), or a histone deacetylase (e.g. HDAC1, HDAC2, HDAC 3, HDAC4, HDAC5, HDAC6, HDAC7, HDAC8, HDAC9, HDAC10, HDAC11, SIRT1, SIRT2, SIRT3, SIRT4, SIRT5, SIRT6, or SIRT7). The histone editor can comprise a yeast, eukaryotic, mammalian, or human histone editor.

In one aspect, the present disclosure provides a vector comprising the nucleic acid described herein. In some cases, the vector further comprises a nucleic acid encoding an engineered guide ribonucleic acid structure. The engineered guide ribonucleic acid structure may be configured to form a complex with the endonuclease. In some cases, the engineered guide ribonucleic acid structure comprises a guide ribonucleic acid sequence. In some cases, the guide ribonucleic acid sequence is configured to hybridize to a target deoxyribonucleic acid sequence. In some cases, the engineered guide ribonucleic acid structure comprises a tracr ribonucleic acid sequence. In some cases, the tracr ribonucleic acid sequence is configured to bind to the endonuclease. In some cases, the vector is a plasmid, a minicircle, a CELiD, an adeno-associated virus (AAV) derived virion, or a lentivirus.

In one aspect, the present disclosure provides a cell comprising any of the vectors described herein.

In one aspect, the present disclosure provides a method of manufacturing an endonuclease. The method can comprise cultivating any of the cells described herein.

In one aspect, the present disclosure provides a method for binding, cleaving, marking, or modifying a double-stranded deoxyribonucleic acid polynucleotide. The method may comprise contacting the double-stranded deoxyribonucleic acid polynucleotide with an endonuclease. In some cases, the endonuclease is a Cas endonuclease. In some cases, the endonuclease is a class 2 endonuclease. In some cases, the endonuclease is a class 2, type II Cas endonuclease. The endonuclease may complex with an engineered guide ribonucleic acid structure. In some cases, the engineered guide ribonucleic acid structure is configured to bind to the endonuclease and the double-stranded deoxyribonucleic acid polynucleotide. In some cases, the double-stranded deoxyribonucleic acid polynucleotide comprises a protospacer adjacent motif (PAM). In some cases, the endonuclease has a molecular weight of about 120 kDa or less, about 110 kDa or less, about 100 kDa or less, about 90 kDa or less, about 80 kDa or less, about 70 kDa or less, about 60 kDa or less, about 50 kDa or less, about 40 kDa or less, about 30 kDa or less, about 20 kDa or less, or about 10 kDa or less. In some cases, the endonuclease comprises a variant with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, or 617-668.

In one aspect, the present disclosure provides a method for binding, cleaving, marking, or modifying a double-stranded deoxyribonucleic acid polynucleotide. The method may comprise contacting the double-stranded deoxyribonucleic acid polynucleotide with an endonuclease. In some cases, the endonuclease is a Cas endonuclease. In some cases, the endonuclease is a class 2 endonuclease. In some cases, the endonuclease is a class 2, type II Cas endonuclease. The endonuclease may complex with an engineered guide ribonucleic acid structure. In some cases, the engineered guide ribonucleic acid structure may be configured to bind to the endonuclease and the double-stranded deoxyribonucleic acid polynucleotide. In some cases, the double-stranded deoxyribonucleic acid polynucleotide comprises a protospacer adjacent motif (PAM). In some cases, the PAM is NGG. In some cases, the endonuclease comprises a variant with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, or 617-668.

In some cases, the endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some cases, the endonuclease is derived from an uncultivated microorganism. In some cases, the double-stranded deoxyribonucleic acid polynucleotide is a prokaryotic, archaeal, bacterial, eukaryotic, plant, fungal, mammalian, rodent, or human double-stranded deoxyribonucleic acid polynucleotide. In some cases, the double-stranded deoxyribonucleic acid polynucleotide is a prokaryotic, archaeal, or bacterial double-stranded deoxyribonucleic acid polynucleotide from a species other than a species from which the endonuclease is derived.

In one aspect, the present disclosure provides a method of modifying a target nucleic acid locus. The method may comprise delivering to the target nucleic acid locus the engineered nuclease system described herein. In some cases, the endonuclease is configured to form a complex with the engineered guide ribonucleic acid structure. In some cases, the complex is configured such that upon binding of the complex to the target nucleic acid locus, the complex modifies the target nucleic locus. In some cases, modifying the target nucleic acid locus comprises binding, nicking, cleaving, or marking the target nucleic acid locus.

In some cases, the target nucleic acid locus comprises deoxyribonucleic acid (DNA) or ribonucleic acid (RNA). In some cases, the target nucleic acid comprises genomic eukaryotic DNA, viral DNA, or bacterial DNA. In some cases, the target nucleic acid comprises bacterial DNA. The bacterial DNA may be derived from a bacterial species different to a species from which the endonuclease was derived. In some cases, the target nucleic acid locus is in vitro. In some cases, the nucleic acid locus is within a cell. In some cases, the endonuclease and the engineered guide nucleic acid structure are provided encoded on separate nucleic acid molecules. In some cases, the cell is a prokaryotic cell, a bacterial cell, a eukaryotic cell, a fungal cell, a plant cell, an animal cell, a mammalian cell, a rodent cell, a primate cell, or a human cell. In some cases, the cell is derived from a species different to a species from which the endonuclease is derived.

In some cases, delivering the engineered nuclease system to the target nucleic acid locus comprises delivering the nucleic acid described herein or the vector described herein. In some cases, delivering the engineered nuclease system to the target nucleic acid locus comprises delivering a nucleic acid comprising an open reading frame encoding the endonuclease. In some cases, the nucleic acid comprises a promoter to which the open reading frame encoding the endonuclease is operably linked. In some cases, delivering the engineered nuclease system to the target nucleic acid locus comprises delivering a capped mRNA containing the open reading frame encoding said endonuclease. In some cases, delivering the engineered nuclease system to said target nucleic acid locus comprises delivering a translated polypeptide.

In some cases, delivering the engineered nuclease system to the target nucleic acid locus comprises delivering a deoxyribonucleic acid (DNA) encoding the engineered guide ribonucleic acid structure operably linked to a ribonucleic acid (RNA) pol III promoter. In some cases, the endonuclease induces a single-stranded break or a double-stranded break at or proximal to the target locus.

Systems of the present disclosure may be used for various applications, such as, for example, nucleic acid editing (e.g., gene editing), binding to a nucleic acid molecule (e.g., sequence-specific binding). Such systems may be used, for example, for addressing (e.g., removing or replacing) a genetically inherited mutation that may cause a disease in a subject, inactivating a gene in order to ascertain its function in a cell, as a diagnostic tool to detect disease-causing genetic elements (e.g. via cleavage of reverse-transcribed viral RNA or an amplified DNA sequence encoding a disease-causing mutation), as deactivated enzymes in combination with a probe to target and detect a specific nucleotide sequence (e.g. sequence encoding antibiotic resistance int bacteria), to render viruses inactive or incapable of infecting host cells by targeting viral genomes, to add genes or amend metabolic pathways to engineer organisms to produce valuable small molecules, macromolecules, or secondary metabolites, to establish a gene drive element for evolutionary selection, to detect cell perturbations by foreign small molecules and nucleotides as a biosensor.

EXAMPLES

Example 1.—Discovery of New Cas Effectors by Metagenomics

Metagenomic Mining

Metagenomic samples were collected from sediment, soil and animal. Deoxyribonucleic acid (DNA) was extracted with a Zymobiomics DNA mini-prep kit and sequenced on an Illumina HiSeq® 2500. Samples were collected with consent of property owners. DNA was extracted from samples using either the Qiagen DNeasy® PowerSoil Kit or the ZymoBIOMICS® DNA Miniprep Kit. DNA was sent for sequencing library preparation (Illumina TruSeq) and sequencing on an Illumina HiSeq® 4000 or Novaseq to the Vincent J. Coates Genomics Sequencing Laboratory at UC Berkeley (paired 150 base pair (bp) reads with a 400-800 bp target insert size). Additionally, publicly available high temperature, as well as soil and ocean metagenomic sequencing data were downloaded from the NCBI SRA. Sequencing reads were trimmed using BBMap (Bushnell B., sourceforge.net/projects/bbmap/) and assembled with Megahit (paperpile.com/c/QSZG6K/c1Mrh). Protein sequences were predicted with Prodigal (paperpile.com/c/QSZG6K/BJ6oW). HMM profiles of known Type II CRISPR nucleases were built and searched against all predicted proteins using HMMER3 (hmmer.org). CRISPR arrays were predicted on assembled contigs with Minced (github.com/ctSkennerton/minced or paperpile.com/c/QSZG6K/OPC44). Taxonomy was assigned to proteins with Kaiju paperpile.com/c/QSZG6K/nMi6k and contig taxonomy was determined by finding the consensus of all encoded proteins.

Predicted and reference (e.g. SpCas9, SaCas9, and AsCas9) Type II effector proteins were aligned with MAFFT (paperpile.com/c/QSZG6K/sVHNH) and phylogenetic trees were inferred using FastTree2 (paperpile.com/c/QSZG6K/osZNM). Novel families were identified from clades composed of sequences recovered from this study. From within families, candidates were selected if they contained all necessary components for laboratory analysis (i.e. they were found on a well-assembled and annotated contig with a CRISPR array). Selected representative and reference sequences were aligned using MUSCLE (paperpile.com/c/QSZG6K/ITO1a) to identify catalytic and PAM interacting residues.

This metagenomic workflow resulted in the delineation of the SMART (SMall ARchaeal-associaTed) endonuclease systems described herein.

Discovery of SMART Endonucleases Containing Active Residue Signatures

Mining of tens of thousands of high quality CRISPR Cas systems assembled from metagenomic data uncovered novel effectors containing both RuvC and HNH domains, but that were of unusually small size (<900 aa). These effector nucleases showed only low sequence similarity (<20% amino acid identity) to archaeal Cas9 endonucleases as a reference point. Phylogenetic analysis of effector protein sequences indicated that the SMART systems are a divergent group relative to well-studied Type II systems from subtype A, B, or C (FIG. 1A).

Figure 2:
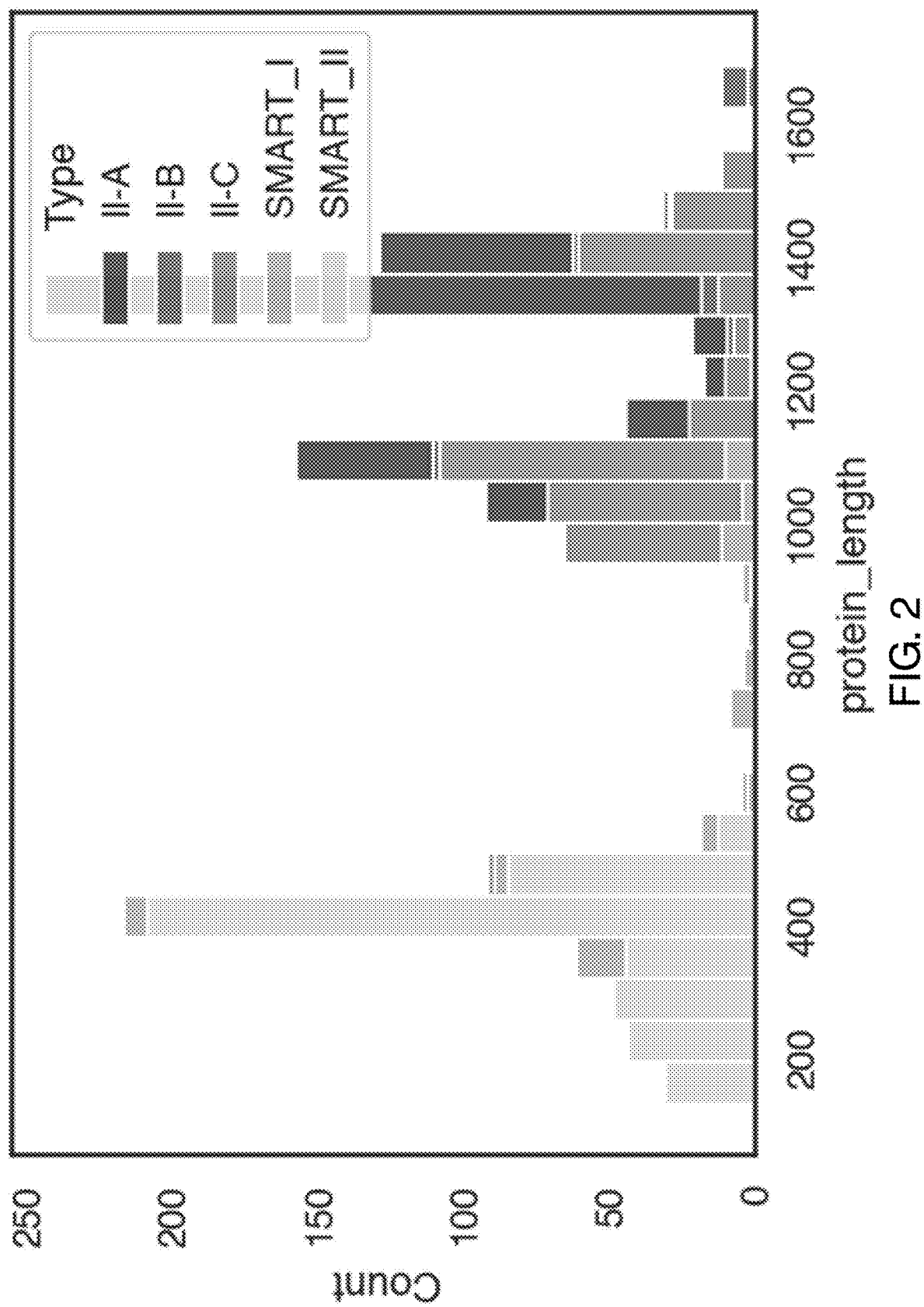
FIG. 2 shows length distribution for SMART effectors described herein, showing that SMART I and II enzymes are clustered at a lower molecular weight than Cas9-like enzymes. SMART nucleases show a bimodal distribution with one peak around 400 aa (SMART II) and a second peak around 750 aa (SMART I). Cas9 nucleases also show a bimodal distribution with peaks around 1,100 aa (e.g. SaCas9) and 1,300 aa (e.g. SpCas9).
Figures 3A, 3B:
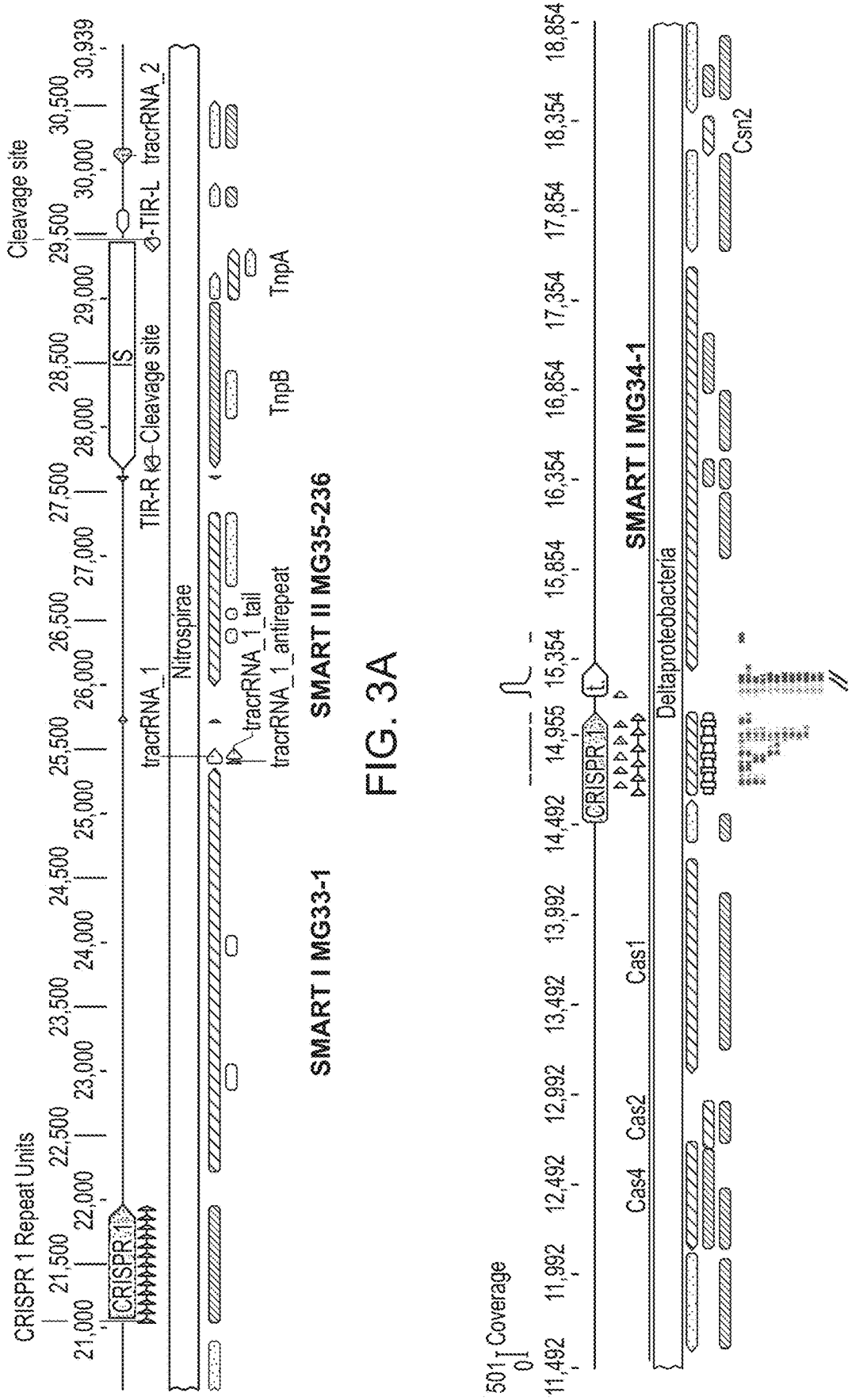
FIGS. 3A-3D depicts the genomic context of 'small' Type II nucleases MG33-1, MG35-236. SMART nucleases and CRISPR accessory proteins are shown as dark grey arrows, other genes are depicted as light grey arrows. Domains predicted for all genes in a genomic fragment are shown as grey boxes under the arrows. Shown are.
Figure 3C:
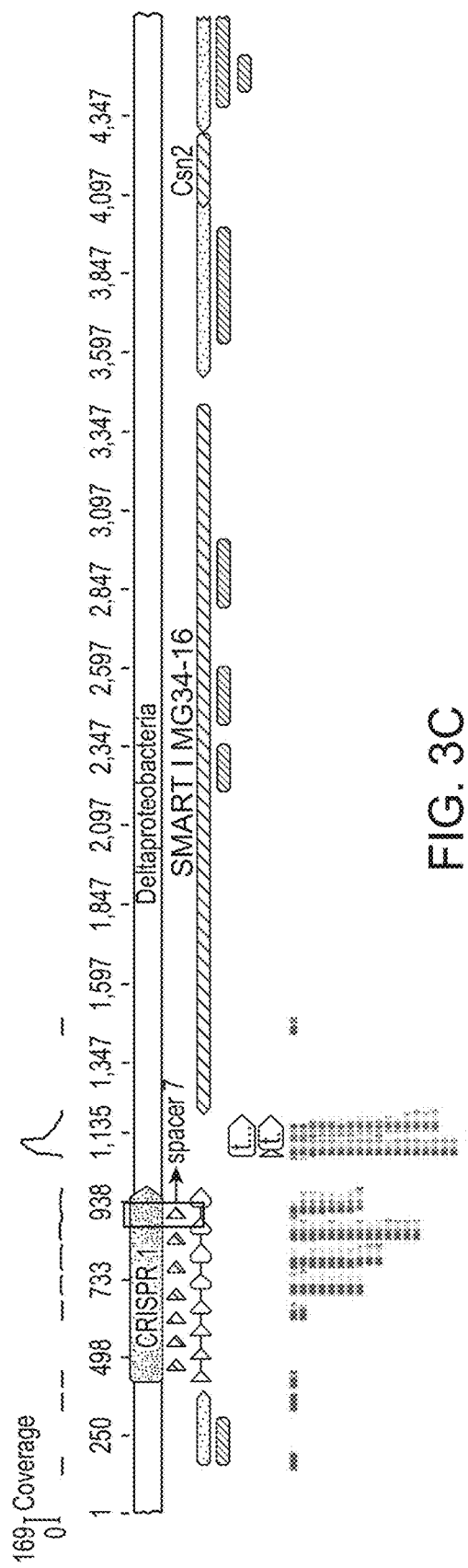
Figure 3D:
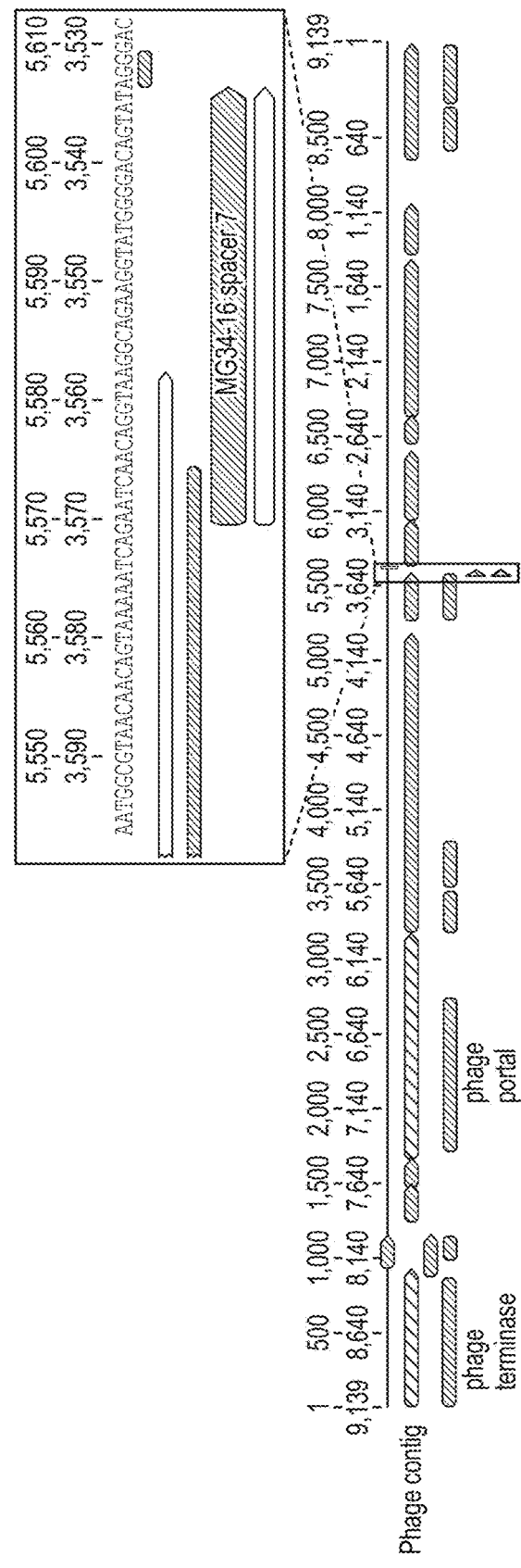
Figure 4A:
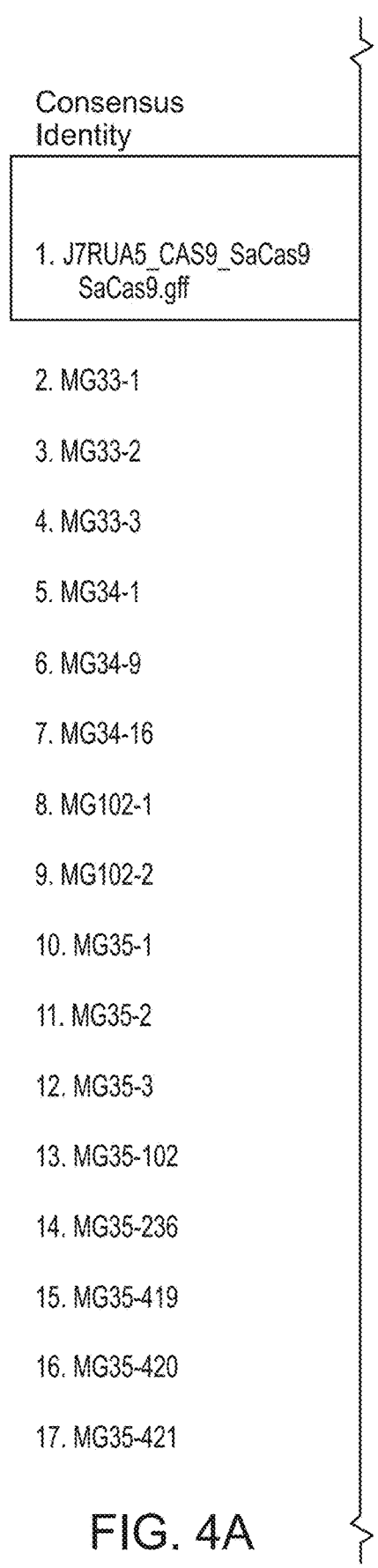
FIGS. 4A-4C show a multiple sequence alignment of example SMART endonucleases (MG33-1 (SEQ ID NO: 1), MG33-2 (SEQ ID NO: 463), MG33-3 (SEQ ID NO: 464), MG34-1 (SEQ ID NO: 2), MG 34-9 (SEQ ID NO: 10), MG34-16 (SEQ ID NO: 17), MG 102-1 (SEQ ID NO: 581), MG102-2 (SEQ ID NO: 582), MG35-1 (SEQ ID NO: 25), MG 35-2 (SEQ ID NO: 26), MG 35-3 (SEQ ID NO: 27), MG 35-102 (SEQ ID NO: 126), MG35-236 (SEQ ID NO: 284), MG35-419 (SEQ ID NO: 222), MG35-420 (SEQ ID NO: 223), and MG 35-421 (SEQ ID NO: 224)), where the sequence of SaCas9 was used as reference domains are shown as a rectangles below the reference sequence, and catalytic residues are shown as squares above each sequence. Shown are.
Figure 4A:
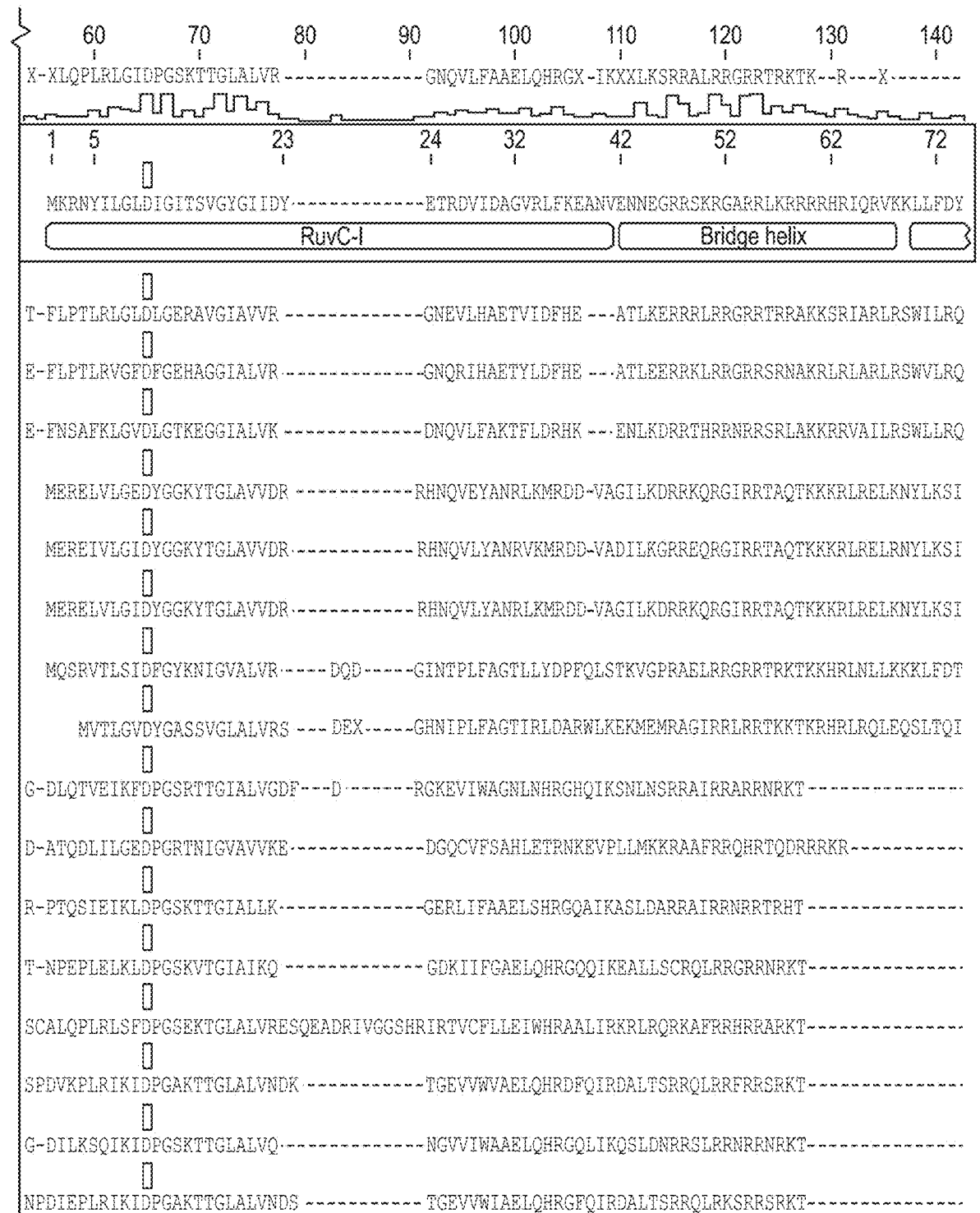
Figure 4B:
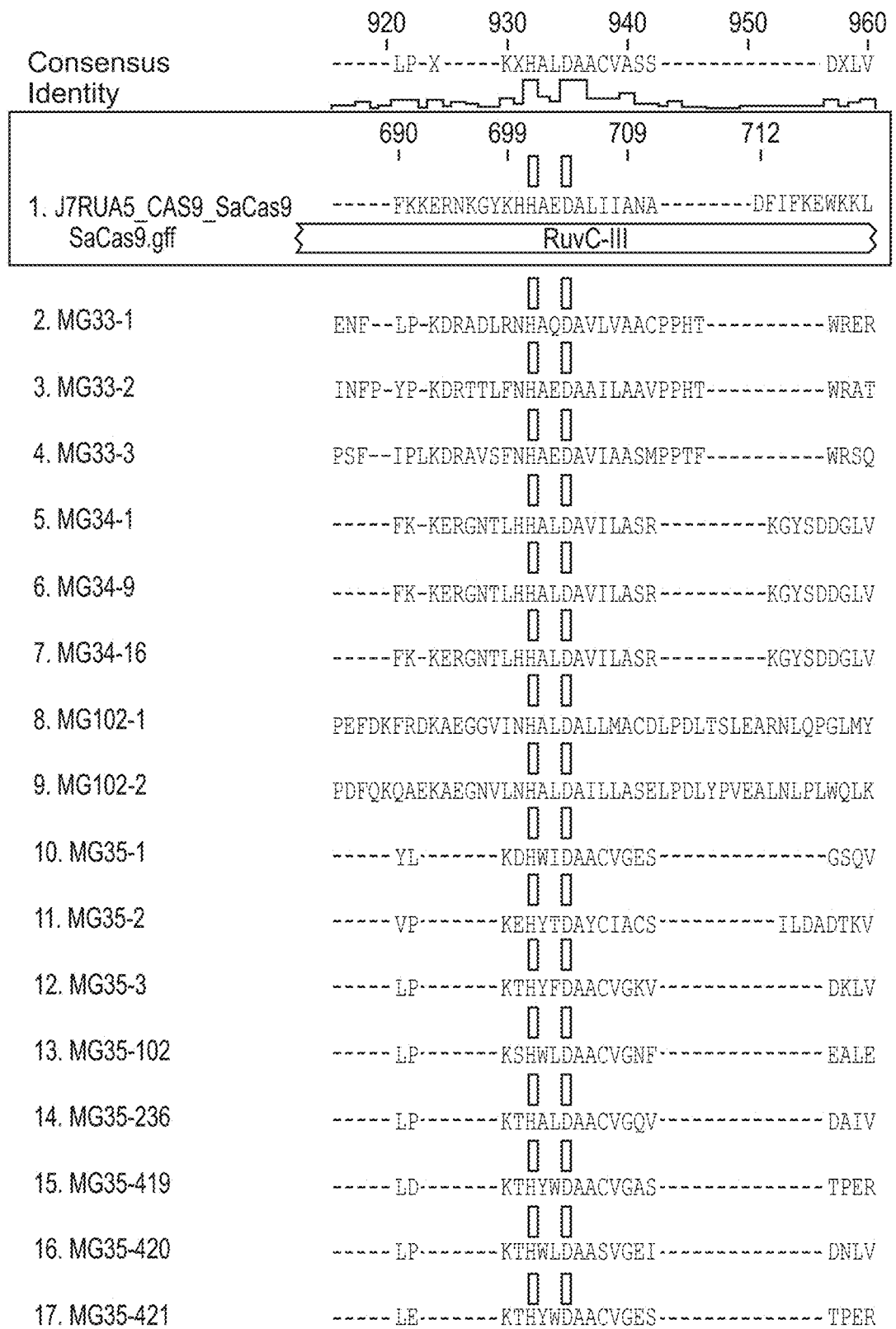
Figure 4C:
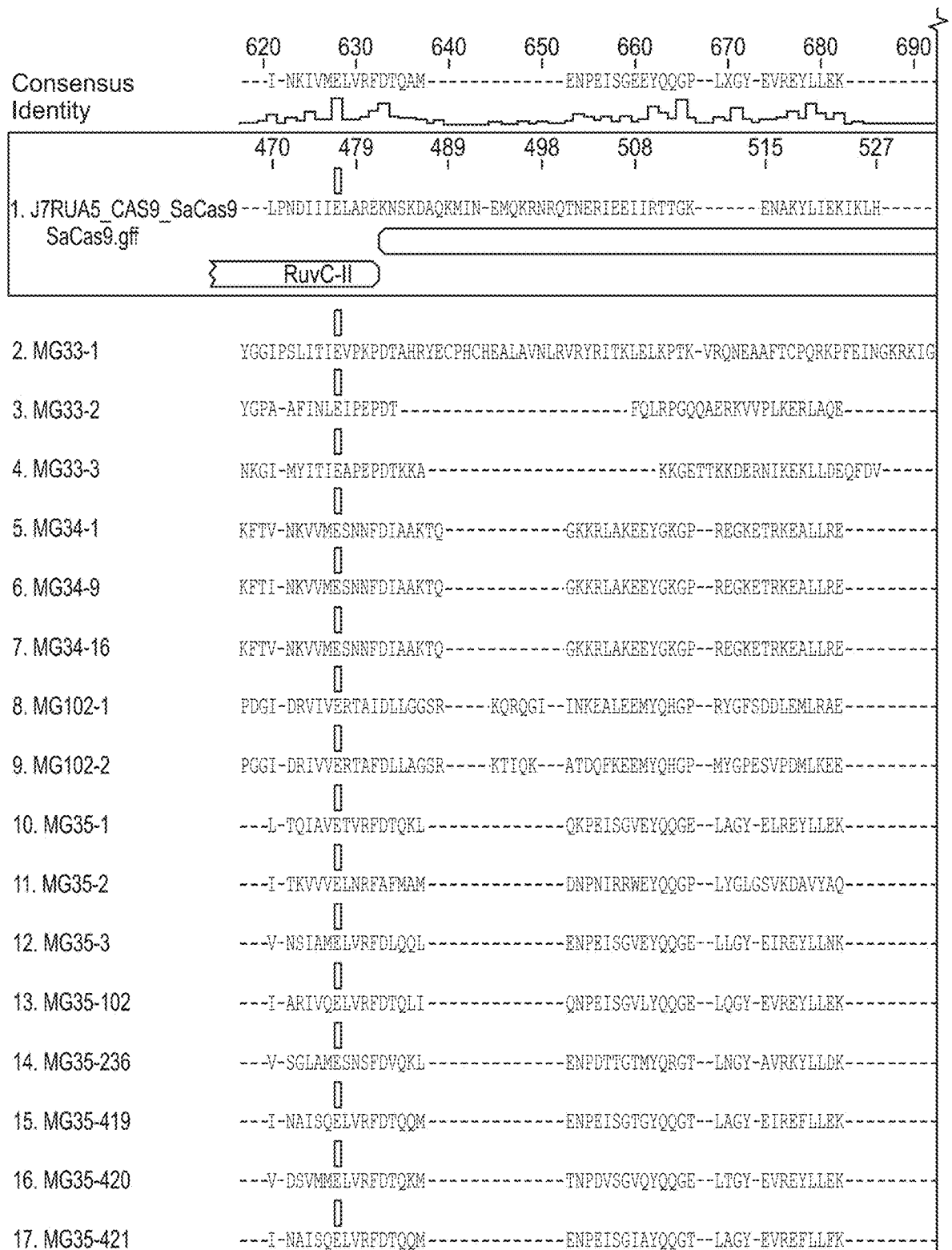
Figure 4C:
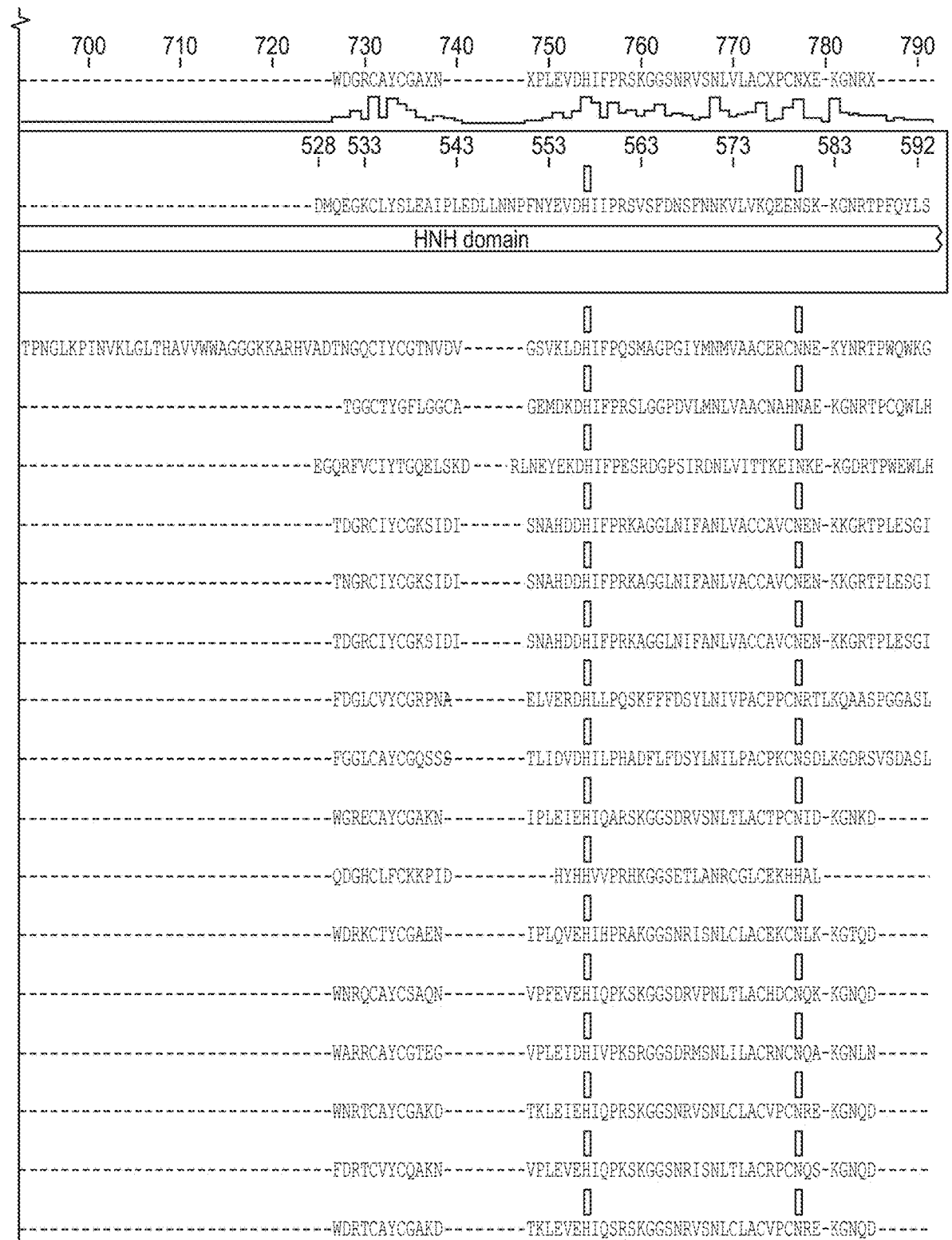

These compact "SMART" effectors (~400-1000 amino acids, FIG. 2) appeared in loci in the genome adjacent to CRISPR arrays. Some of these adjacent SMART loci also included sequences predicted to encode tracrRNAs and the CRISPR adaptation genes (e.g. genes involved in spacer acquisition) cas1, cas2, and/or cas4 within the same operon (FIGS. 3A-3D). Despite their compact size, SMART effectors contain six putative HNH and RuvC catalytic residues when aligned with a reference SaCas9 sequence (FIG. 4A-C). In addition, 3D structure predictions identified residues involved in guide and target binding, as well as in recognition of a PAM, suggesting that that the SMART effectors are active dsDNA endonucleases.

Multiple Groups of SMART Endonucleases

Figures 5A, 5B:
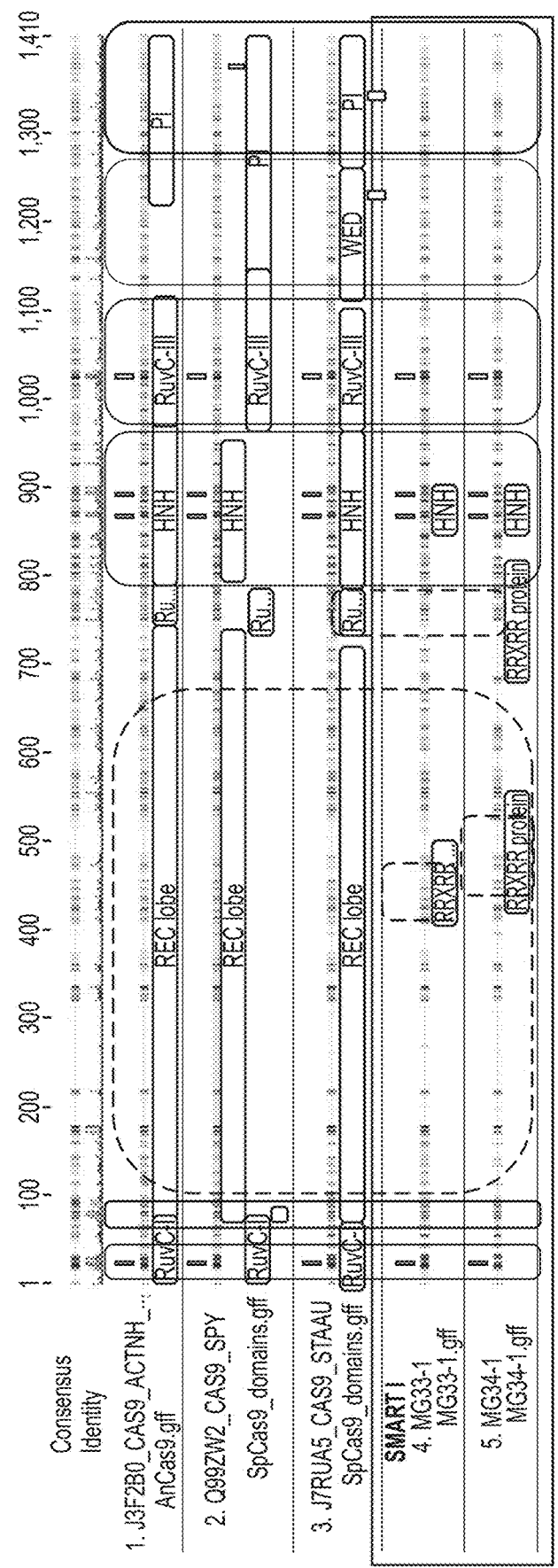
FIGS. 5A-5B depict an example domain organization for SMART I endonucleases, using MG34-1 as an example. Shown are (FIG. 5A) a diagram showing the predicted domain architecture of SMART I nucleases consisting of three RuvC domains, a bridge helix ("BH"), a domain with homology to a Pfam PF14239 which interrupts a recognition domain ("REC"), an HNH endonuclease domain ("HNH"), a wedge domain ("WED"), and a PAM interacting domain (PI)
Figures 6A, 6B:
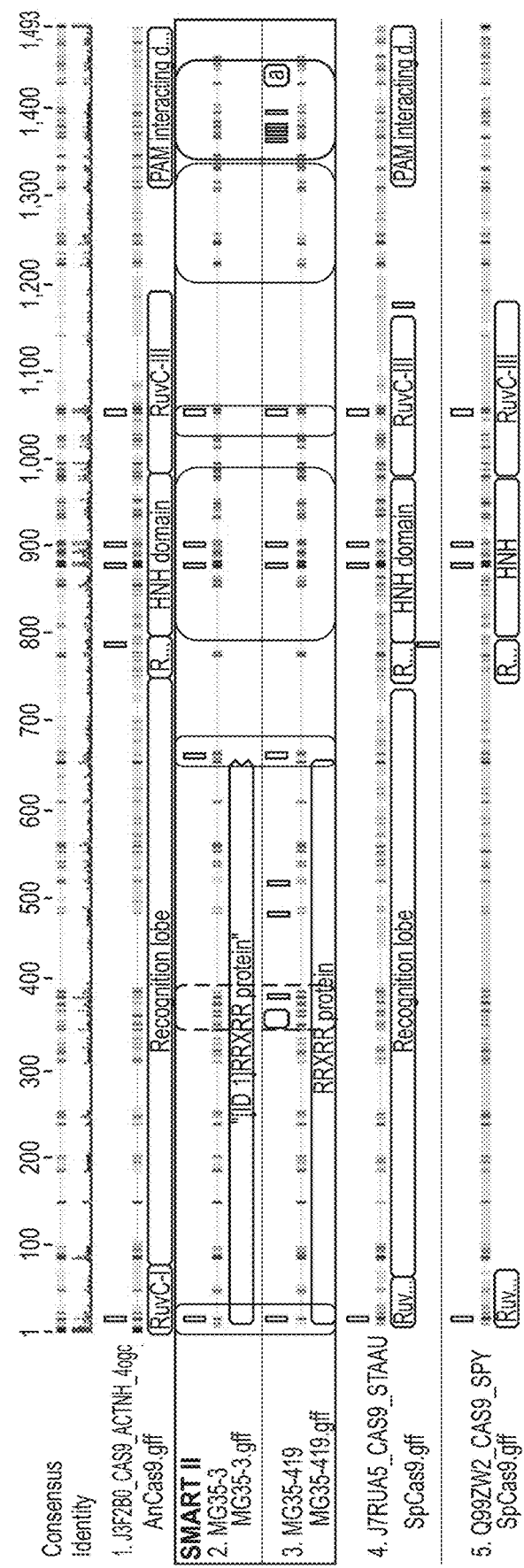
FIGS. 6A-6B depict an example domain organization for SMART II endonucleases, using MG35 family enzymes (MG35-3, MG35-4) as an example. Shown are (FIG. 6A) a diagram showing the predicted domain architecture of SMART II nucleases consist of three RuvC domains, a domain with homology to a Pfam PF14239, an HNH endonuclease domain, an unknown domain, and a recognition domain (REC)
Figure 7B:
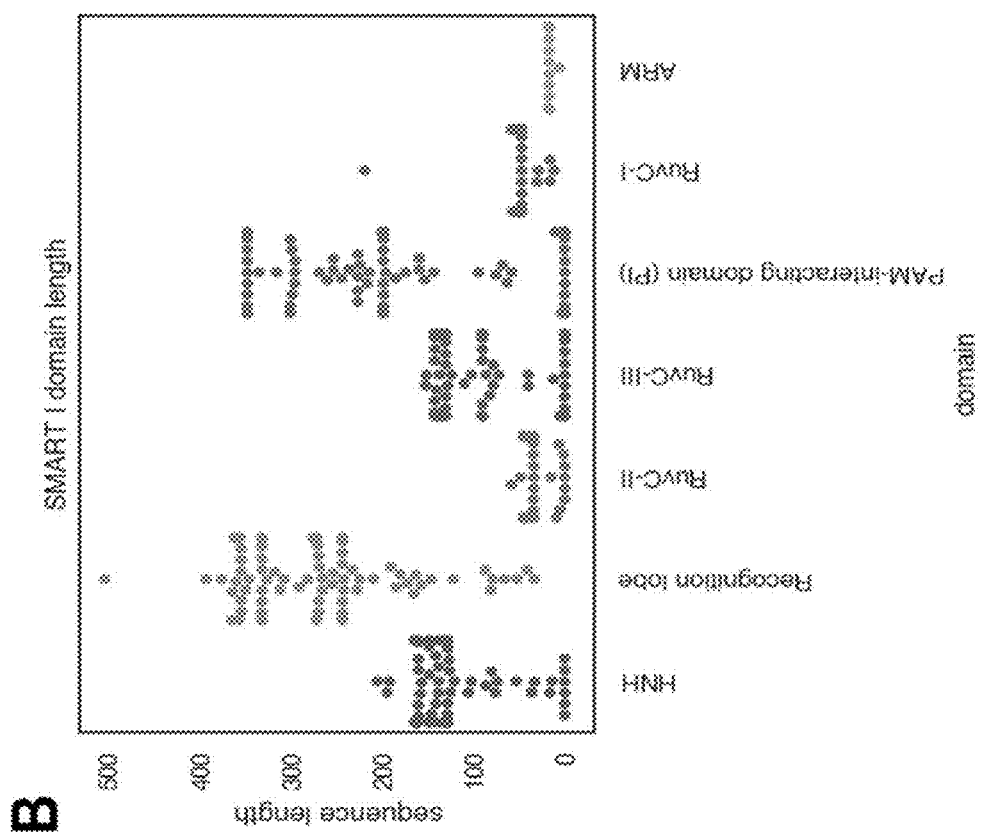
FIGS. 7A-7B illustrate various features of SMART enzymes. Shown are (FIG. 7A) a dot plot showing identity of SMART I domains of various enzymes depicted herein versus those of spCas9 showing that these have a maximum of about 35% sequence identity.
Figure 7A:
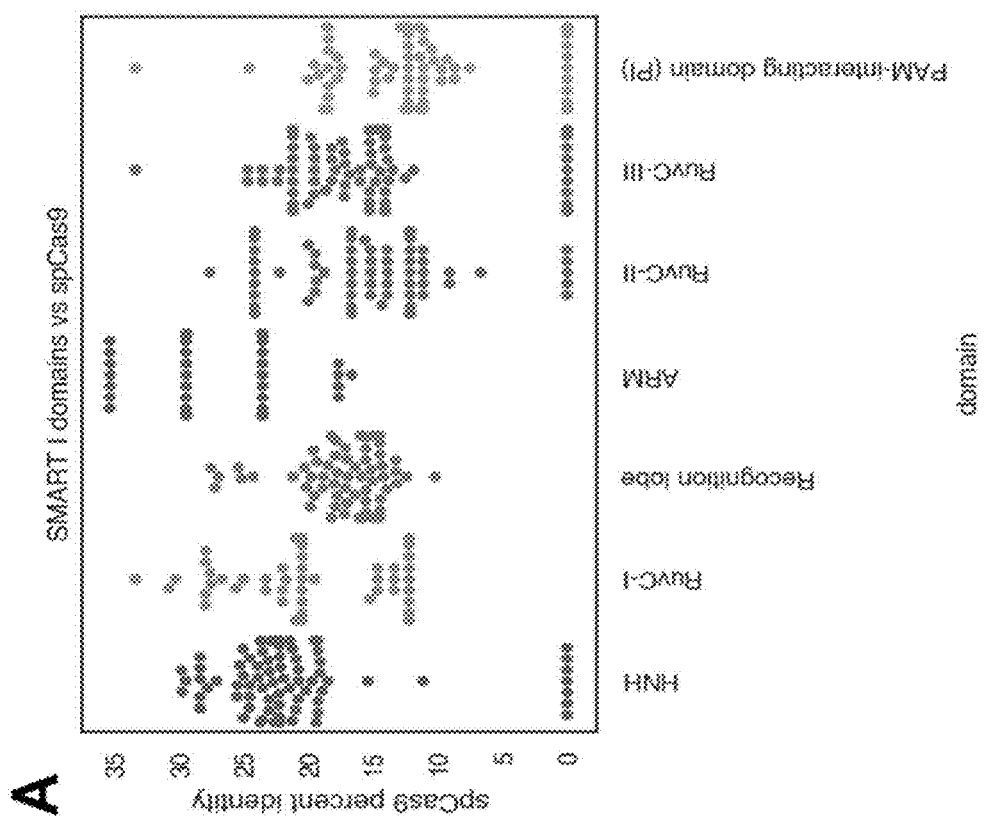
Figures 8A, 8B:
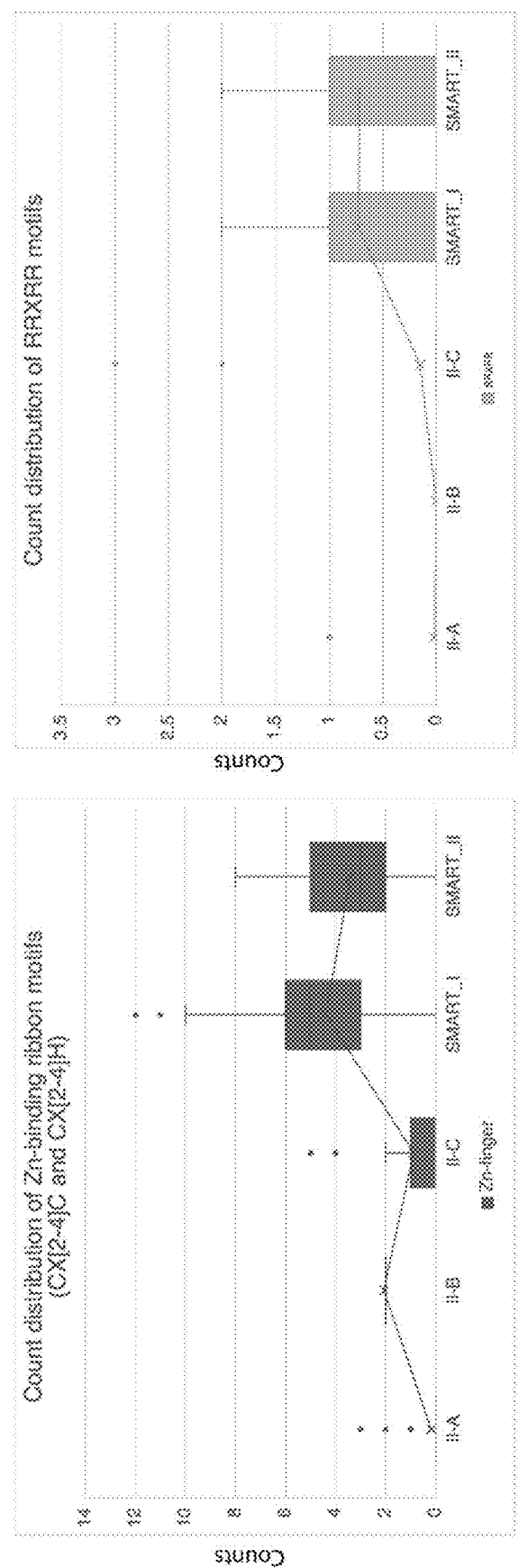
FIGS. 8A-8B illustrates count distribution of various SMART-specific motifs versus motifs predicted in Cas9 nuclease sequences showing that these motifs occur more commonly in SMART enzymes; motifs were predicted on 803 reference Cas9 sequences (Type II-A, II-B, and II-C), 84 SMART I sequences, and 471 SMART II sequences. Shown are (FIG. 8A) a box plot of count frequency of Zn-binding ribbon motifs (CX[2-4]C and CX[2-4]H) in various types of class 2 Cas enzymes.
Figure 9A:
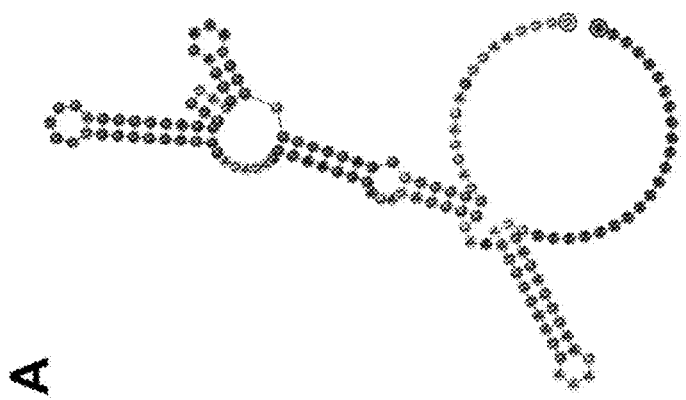
FIGS. 9A-9D illustrates predicted guide RNA structures of designed single-guide RNAs (sgRNAs) for cleavage activity with SMART I endonucleases. Shown are (FIG. 9A) MG34-1 sgRNA 1.
Figure 9B:
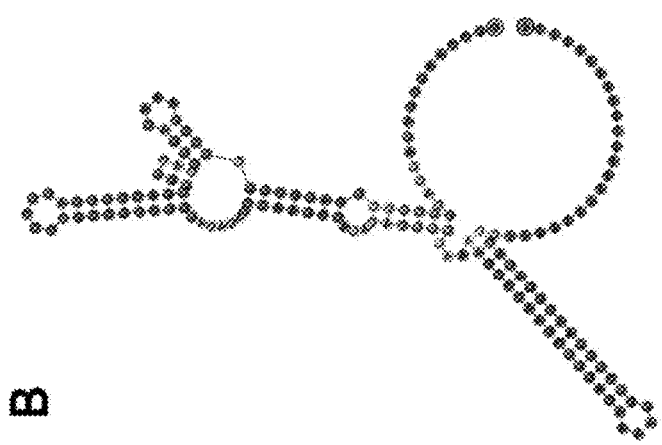
Figure 9C:
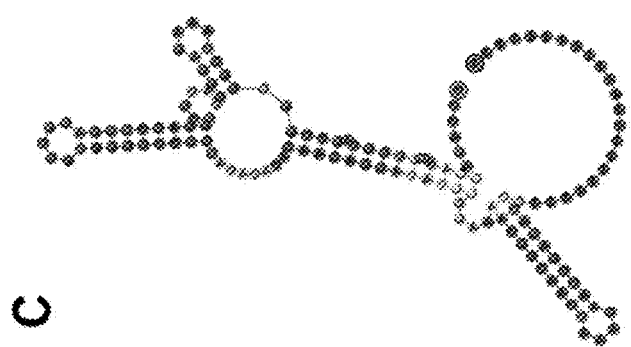
Figure 9D:

Based on the location of important catalytic and binding residues, SMART nucleases comprise three RuvC domains, an arginine rich region usually containing an RRxRR motif (e.g. a domain with PF14239 homology), an HNH endonuclease domain, and a putative recognition domain (FIGS. 5A-5B and FIGS. 6A-6B). These domains share low sequence similarity with reference sequences (FIGS. 7A-7B). In addition, SMART effectors, as well as reference archaeal sequences, contain RRxRR and zinc-binding ribbon motifs (CX[2-4]C or CX[2-4]H) significantly more frequently than Cas9 nucleases (FIGS. 8A-8B). In addition, unlike Cas9 effector sequences, most SMART effectors contain significant hits to the Pfam domain PF14239, which is often associated with diverse endonucleases. Based upon differences in SMART effector size, phylogenetic relationship, and both operon and domain architecture, we classified these systems into two primary groups: SMART I and SMART II. The salient features of these groups are outlined in Table 3 below, which also illustrates differences compared to Class 2, Type II A/B/C Cas enzymes.

TABLE 3

Attributes of SMART I and II group enzymes described herein

| Attribute | SMART I | SMART II | Type II: A, B, C |
|---|---|---|---|
| Zn-binding residues | yes | yes | no |
| Bridge helix | yes | no | yes |
| PAM interacting and | yes | no | yes |
| | WED domain | | |
| RRxRR motif | yes | yes | no |
| REC domain | Novel domain w/ homology to PF14239 | Novel domain at C-terminus | Cas9 REC domain |
| Domain w/ PF14239 homology | yes | yes | no |
| Monophyletic clade | yes | no | yes |
| Related to TnpB | yes | yes | yes |
| Operon contains IS605 Tns repeats | no | sometimes | no |
| <900 aa | sometimes | yes | no |
| CRISPR-associated | yes | sometimes | yes |
| Contains RuvC and HNH | yes | yes | yes |

SMART I Endonucleases

SMART I effectors range between approximately 700 amino acids and 1,050 amino acids in size. Common features in their genomic context were adaptation module genes (e.g. genes involved in spacer acquisition) and predicted tracrRNAs near the CRISPR array, the organization of which resembled Type II and Type V CRISPR systems (FIGS. 3A, 3B and 3C). The RRXRR motif-containing region in SMART I effectors is unique but may play a similar functional role as the arginine-rich bridge helix in Cas9 nucleases. When modeled against the SaCas9 crystal structure, predicted 3D structures of SMART I effectors showed unaligned regions within the recognition lobe (which often contains the Pfam domain PF14239) and RuvC-II domains (FIGS. 5A-5B). The results indicated that these domains have different origins relative to other Type II effectors. Taken together with their divergent placement in a Type II effector phylogenetic tree and their low sequence similarity to known Type II effectors (FIG. 1A), these results indicate that SMART I endonucleases belong to a new group of Type II CRISPR systems. Following the accepted classification of CRISPR systems, these SMART I systems were classified as Type II-D.

Putative single guide RNAs (sgRNAs) were engineered using environmental RNA expression data for the SMART I MG34-1 system. In addition, multiple sgRNAs designed from SMART I repeat and tracrRNA predictions were tested in vitro in PAM enrichment assays. In the case of SMART I enzymes, optimal identification of PAM sequences was performed using end repair and blunt-end ligation at this step, suggesting that these enzymes can produce staggered double-stranded DNA breaks. Assays confirmed dsDNA cleavage for MG34-1 (SEQ ID NO: 2), MG34-9 (SEQ ID NO: 9), and MG34-16 (SEQ ID NO: 17) with multiple sgRNA designs (FIGS. 7A-7B, depicting use of SEQ ID NOs: 612-615). MG34-1 demonstrated a preference for an NGGN PAM for target recognition and cleavage (FIG. 8A). Analysis of the cut site indicated preferential cleavage at position 7 (FIG. 8B). These results suggest a novel biochemical mechanism compared with cleavage mechanisms from other Type II enzymes, which preferentially cleave at positions 2-3 from the PAM, supporting a new classification for SMART I CRISPR systems.

Environmental expression data for some SMART I systems confirmed in situ transcription of the CRISPR array and intergenic region encoding the predicted tracrRNA (FIGS. 3B and 3C). Additionally, cases of active CRISPR targeting were evaluated by searching spacer sequences that match other genomic sequences assembled from the same, or related metagenomes. Along these lines, a phage genome being targeted by one of the spacers encoded in a SMART I CRISPR array (FIGS. 3C and 3D) was identified. Analysis of the region adjacent to the target sequence suggests a 3' PAM sequence containing a GG motif (FIG. 3D). These results indicate that SMART I CRISPR systems are active in their natural environments as RNA guided effectors involved in phage defense, likely functioning as nucleases that cut or degrade targeted DNA or RNA.

SMART I Effectors are Active, RNA Guided dsDNA CRISPR Endonucleases

Figures 10A, 10B:
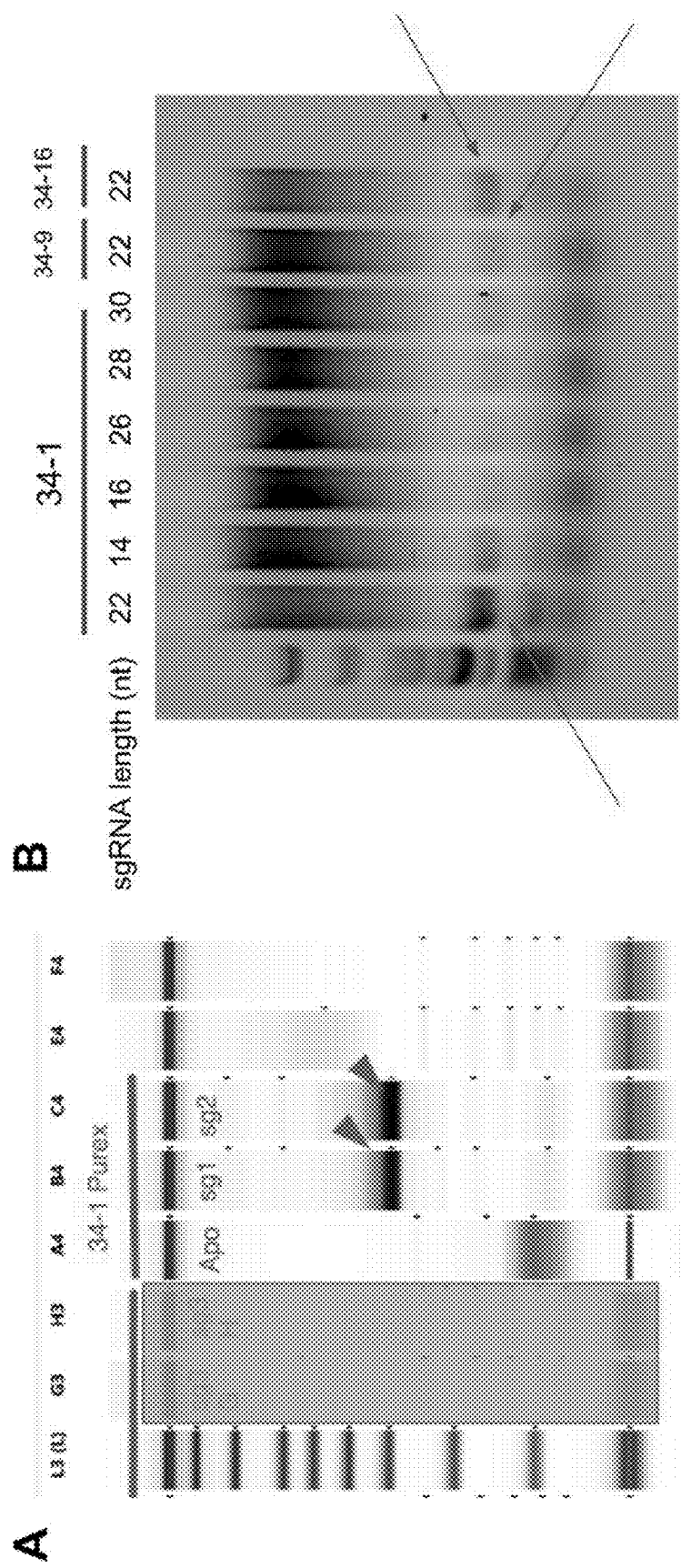
FIGS. 10A-10B depict cleavage characterization of SMART I nucleases as described in Example 1.
Figure 11A:
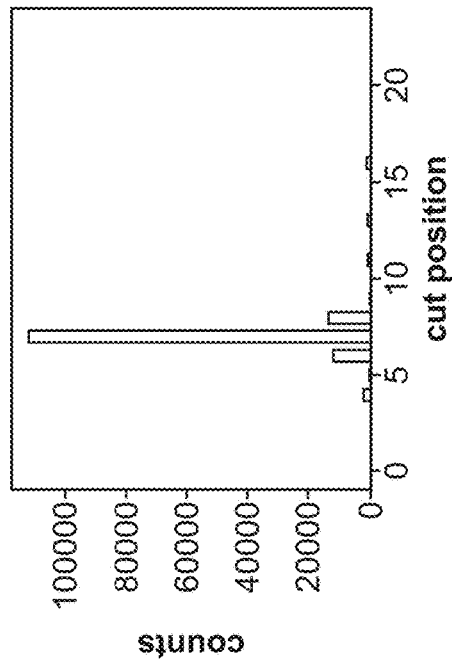
FIGS. 11A-11C illustrate sequence cutting preference for MG34 nucleases.
Figure 11B:
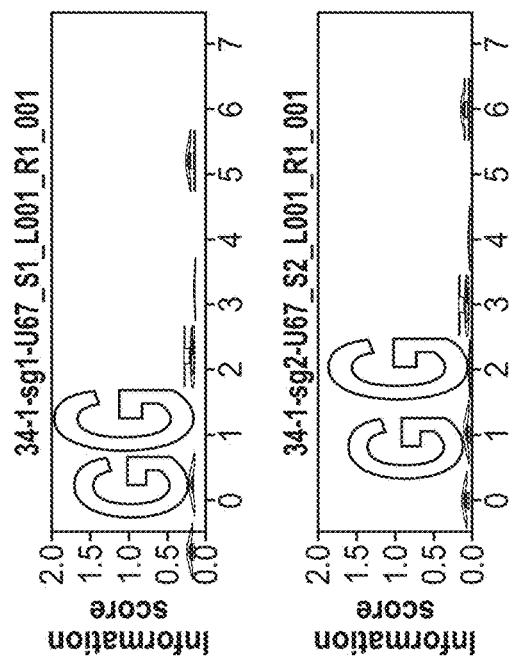
Figure 11C:
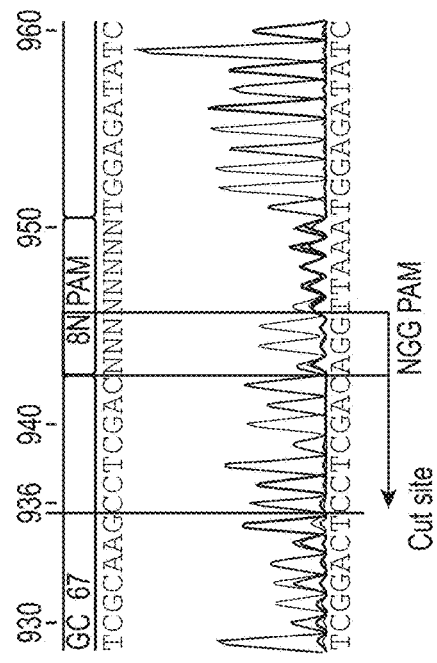

Putative single guide RNA (sgRNA) were engineered using the environmental RNA expression data for SMART I MG34-1 and MG34-16 systems (FIGS. 3B and 3C, and FIGS. 9A-9D). In addition, multiple sgRNAs designed from SMART I repeat and tracrRNA predictions were tested in vitro in PAM enrichment assays (FIGS. 10A-10C). Assays confirmed programmable dsDNA cleavage for MG34-1, MG34-9, and MG34-16 with multiple sgRNA designs (FIGS. 10A-10C). MG34-1 and MG34-9 require an NGGN PAM for target recognition and cleavage (FIGS. 11A and 11C). Analysis of the cut site indicates preferential cleavage at position 7 (FIGS. 11B and 11C). These results suggest a novel biochemical cleavage mechanism compared with Cas9 enzymes, which preferentially cleave at position 3 from the PAM, and provide further support for a new classification for SMART I CRISPR systems.

PAM enrichment assays without an end repair step did not show activity for SMART I nucleases. The requirement for end repair to create blunt-end fragments prior to ligation in the PAM enrichment protocol indicates that these enzymes create a staggered double strand DNA break.

Experiments conducted in *E. coli* showed that the system has the required activity to function as a nuclease in cells. *E. coli* strains expressing MG34-1 and sgRNAs were transformed with a kanamycin resistance plasmid containing a target for the sgRNA. In the presence of the antibiotic, successful targeting and cutting of the antibiotic resistance plasmid will result in a growth defect. The assay showed an approximately 2-fold growth repression compared with control experiments conducted with a kanamycin resistance plasmid that did not contain a target for the sgRNA (FIGS. 12A-12B).

SMART II Endonucleases

SMART II effectors have a size distribution that skews smaller (~400 amino acids-600 amino acids) vs. SMART I effectors. Their genomic context suggested unusual repetitive regions or CRISPR arrays. The non-CRISPR repetitive regions contain direct repeats that range in size from about 10 to over 30 bp. In some cases, these include multiple distinct repeating units. Sometimes, common CRISPR identification algorithms will flag these regions as CRISPR systems; however, closer inspection will reveal that the regions identified as spacer sequences are repeated in the array. The arrays are not immediately adjacent to the effectors, but they are in the same genomic region (FIG. 3A, MG35-236 and FIG. 13A, e.g., >20 kb from the effector gene). SMART II system operons were generally devoid of adaptation module genes (e.g. genes involved in spacer acquisition).

Figure 14:
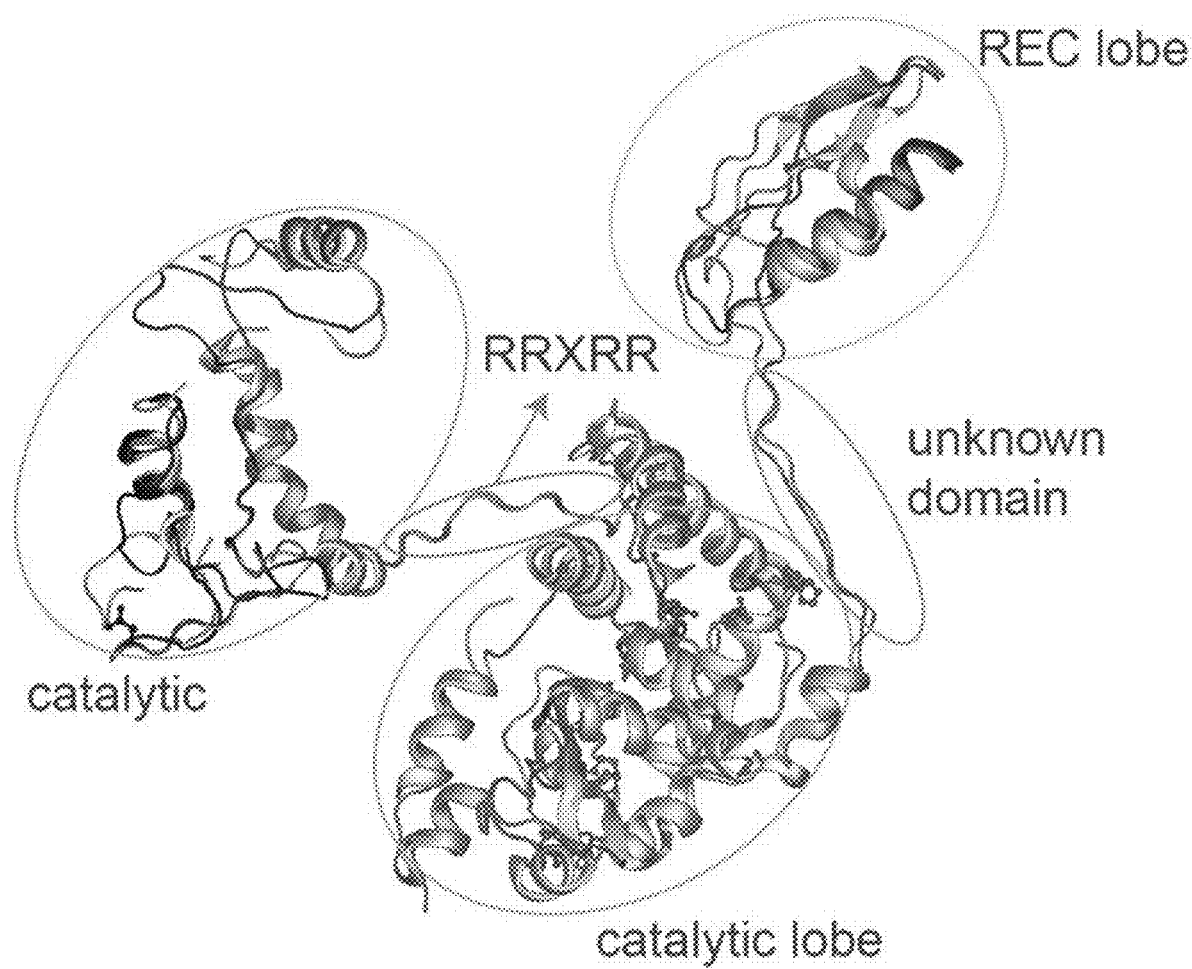
FIG. 14 shows a 3D structural prediction for SMART II MG35-419. This 3D model aligns well with regions of the SaCas9 crystal structure, despite being less than half its size. Regions that aligned with the SaCas9 template include the catalytic lobe (RuvC-I, HNH and RuvC-III domains) and a short region of the recognition (REC) lobe. SMART II-specific domains include a domain containing an RRXRR motif and homology to a Pfam PF14239, and a domain of unknown function.

Structural predictions identified characteristic residues of Cas enzymes involved in guide RNA binding, target cleavage, and recognition of and interaction with a PAM, in addition to all six RuvC and HNH nuclease catalytic residues (FIGS. 6A-6B) often found in class 2, type II Cas effectors. In addition, SMART II effectors contained multiple RRXRR and zinc binding ribbon motifs (CX[2-4]C or CX[2-4]H), which are possibly involved in recognition and binding of a target nucleic acid motif. Based on the location of important residues, the predicted domain architecture of SMART II nucleases consisted of three RuvC subdomains, an arginine-rich region containing an RRxRR motif (e.g. a domain with PF14239 homology), an HNH endonuclease domain, an unknown domain, and a recognition domain (REC) (FIGS. 6A-6B). The domain architecture of SMART II effectors differed from the known domain architecture for Type II Cas9 nucleases (FIGS. 6A-6B and FIG. 14).

Figure 13A:
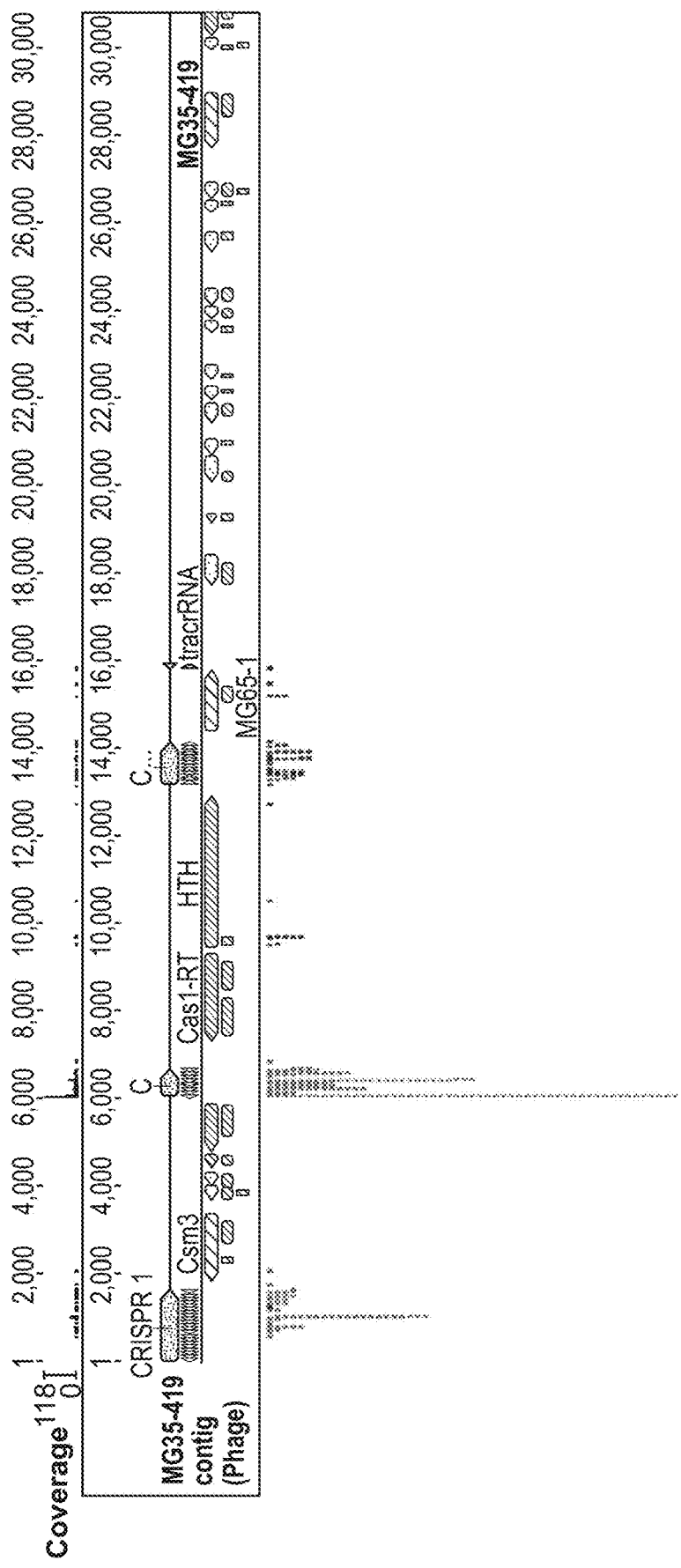
FIGS. 13A-13B show an example genomic context of a SMART system for MG35-419. SMART nucleases are shown as dark grey arrows, other genes are depicted as lighter grey arrows. Domains predicted for all genes in a genomic fragment are shown as grey boxes under the arrows. Environmental expression sequencing reads are shown aligned under the CRISPR arrays in FIG. 13A and upstream from the effector in FIG. 13B. Transcriptomic coverage for the regions showing expression is illustrated above the contig sequence.
Figure 13B:
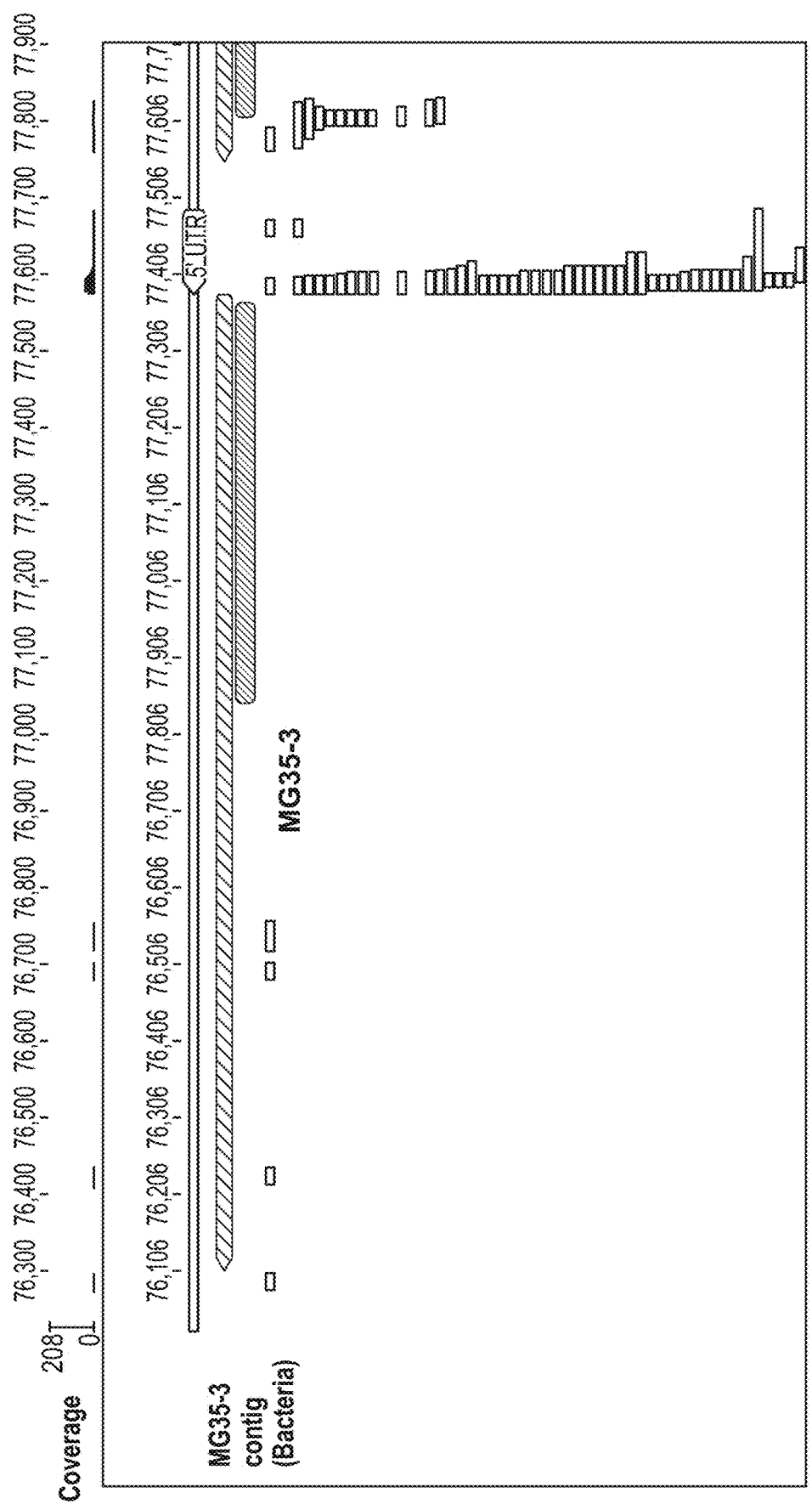

Environmental transcriptomic data for some SMART II systems confirmed in situ expression of CRISPR arrays and other repetitive regions in the natural environment (FIG. 13A). Transcription of the 5' untranslated region (UTR) of some SMART II effectors was also observed from environmental expression data (FIG. 13B), suggesting that this region may be important for either nuclease activity or regulation of the SMART system.

Figure 15:
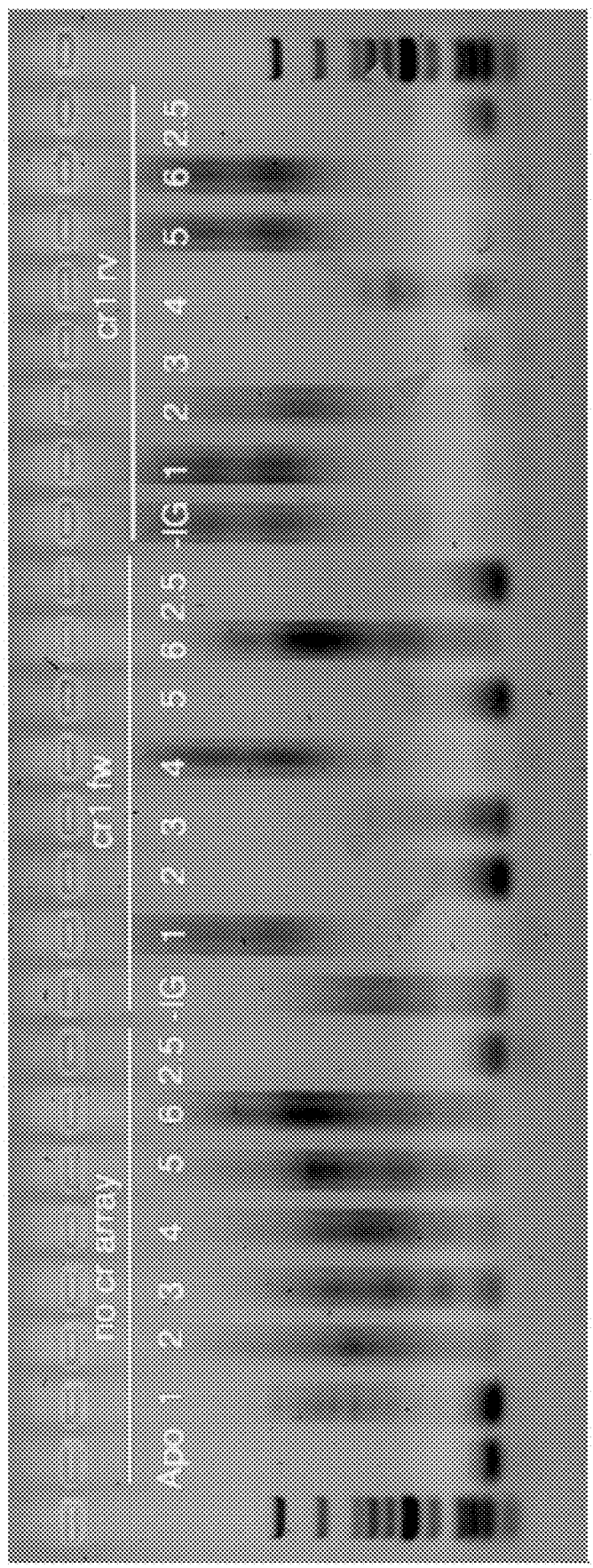
FIG. 15 depicts results of preliminary cleavage assays for SMART II effectors. MG35-420 (SEQ ID NO:223) protein preps were tested for cleavage activity in TXTL extracts where the entire locus was expressed. Experiments incubated the protein prep with a PAM library (dsDNA target), a repetitive region predicted in the locus (crl) in both forward and reverse orientations (fw and rv), and with intergenic regions potentially encoding needed cofactors. Lanes 2-9 (no cr array): control experiments without a repetitive region. Apo: only protein prep with a target PAM library. Labels 1-2.5 represent seven different intergenic regions. -IG: no intergenic region included as control. PCR gel of the ligation products shows putative cleavage bands (arrows) suggesting dsDNA cleavage.

Preliminary in vitro experiments conducted with SMART II effector proteins, repetitive regions, and associated intergenic regions show that these enzymes may have the ability to cleave dsDNA, possibly in a programmable manner (FIG. 15). Results suggest that SMART II nuclease activity may be RNA and/or DNA guided, which may require using a repetitive region such as a CRISPR array, or via recognition of features encoded within the loci such as TIR or 5' UTR.

Some SMART II effectors were observed next to a putative insertion sequence (IS) encoding transposases TnpA and TnpB (FIG. 3A). The ends of the IS were identified as containing terminal inverted repeats (TIR) with predicted hairpin structures, and the target site duplication at which the IS most likely integrated into was also identified). In addition, some SMART II loci encoded putative TIRs flanking the SMART II effector (e.g. FIGS. 3A-3D).

Example 2.—PAM Sequence Identification/Confirmation for the Endonucleases Described Herein Putative SMART endonucleases were expressed in an *E. coli* lysate-based expression system (PURExpress, New England Biolabs). In this system, the endonuclease was codon optimized for *E. coli* and cloned into a vector with a T7 promoter and C-terminal His tag. The gene was PCR amplified with primer binding sites 150 bp upstream and downstream from the T7 promoter and terminator sequences, respectively. This PCR product was added to NEB PURExpress at 5 nM final concentration and expressed for 2 hr at 37° to produce the endonucleases for the PAM assays.

The putative sgRNAs compatible with each SMART Cas enzyme described herein were identified from RNAseq reads assembled to the contig CRISPR locus assembled from sequencing data: secondary structure was determined for the tracr region from RNAseq data along with the repeat sequence from the CRISPR array in the Geneious software package (geneious.com), and the resulting helix was trimmed and concatenated with a GAAA tetra-loop. Multiple lengths of repeat-anti-repeat helix trimming were tested, as well as different spacer lengths and different tracr termination points (FIGS. 12A-12B, which demonstrate SEQ ID NOs: 612-615). Each sgRNA was then assembled via assembly PCR, purified with SPRI beads, and in vitro transcribed (IVT) following manufacturer's recommended protocol for short RNA transcripts (HiScribe® T7 kit, NEB). RNA transcription reactions were cleaned with the Monarch RNA kit and checked for purity via Tapestation® (Agilent).

PAM sequences were determined by sequencing plasmids containing randomly-generated potential PAM sequences that can be cleaved by the putative nucleases. In this system, an E. coli codon optimized nucleotide sequence encoding the putative nuclease was transcribed and translated in vitro from a PCR fragment under control of a T7 promoter. A second PCR fragment with a minimal CRISPR array composed of a T7 promoter followed by a repeat-spacer-repeat sequence was transcribed in the same reaction. Successful expression of the endonuclease and repeat-spacer-repeat sequence in the TXTL system followed by CRISPR array processing provides active in vitro CRISPR nuclease complexes.

A library of target plasmids containing a spacer sequence matching that in the minimal array preceded by 8N mixed degenerate bases (potential PAM sequences) were incubated with the output of the TXTL reaction (10 mM Tris pH 7.5, 100 mM NaCl, and 10 mM $MgCl_2$ with a 5-fold dilution of translated Cas enzyme, 5 nM of an 8N PAM plasmid library, and 50 nM of sgRNA targeting the PAM library). After 1-3 hr, the reaction was stopped, and the DNA was recovered via a DNA clean-up kit. Adapter sequences were blunt-end ligated to DNA with active PAM sequences that had been cleaved by the endonuclease, whereas DNA that had not been cleaved was inaccessible for ligation. DNA segments comprising active PAM sequences were then amplified by PCR with primers specific to the library and the adapter sequence. The PCR amplification products were resolved on a gel to identify amplicons that correspond to cleavage events. The amplified segments of the cleavage reaction were also used as a template for preparation of an NGS library or as a substrate for Sanger sequencing. Sequencing this resulting library, which was a subset of the starting 8N library, revealed sequences with PAM activity compatible with the CRISPR complex. For PAM testing with a processed RNA construct, the same procedure was repeated except that an in vitro transcribed RNA was added along with the plasmid library and the minimal CRISPR array/tracr template was omitted. The following spacer sequence was used as a target in these assays (5'-CGUGAGCCAC-CACGUCGCAAGCCUCGAC-3'; SEQ ID NO: 674).

Having obtained raw sequencing reads from the PAM assays, reads were filtered by Phred quality score >20. The 24 bp representing the known DNA sequence from the backbone adjacent to the PAM was used as a reference to find the PAM-proximal region and the 8 bp adjacent were identified as the putative PAM. The distance between the PAM and the ligated adapter was also measured for each read. Reads that did not have an exact match to the reference sequence or adapter sequence were excluded. PAM sequences were filtered by cut site frequency such that only PAMs with the most frequent cut site ±2 bp were included in the analysis. The filtered list of PAMs was used to generate a sequence logo using Logomaker (Tareen A, Kinney J B. Logomaker: beautiful sequence logos in Python. Bioinformatics. 2020; 36(7):2272-2274, which is incorporated by reference herein).

Example 3.—Protocol for Predicted RNA Folding

Predicted RNA folding of the active single RNA sequence is computed at 37° using the method of Andronescu 2007. The color of the bases corresponds to the probability of base pairing of that base, where red is high probability and blue is low probability.

Example 4.—In Vitro Cleavage Efficiency

Endonucleases are expressed as His-tagged fusion proteins from an inducible T7 promoter in a protease deficient E. coli B strain. The endonuclease was fused to two nuclear localization signals (N-term NLS nucleoplasmin bipartite and C-term simian virus 40 T-antigen NLS PPKKKRK; SEQ ID NOL 675), a maltose binding protein (MBP) tag, a tobacco etch virus (TEV) protease cleavage site, and a 6XHis tag in the following order from N to C termini: 6XHis-MBP-TEV-NLS-gene-NLS-STOP. This protein was expressed under a pTac promoter in NEB Iq E. coli by autoinduction media (MagicMedia ThermoFisher), grown at 30° C., and induced at 16° C.

Cells expressing the His-tagged proteins were lysed by sonication and the His-tagged proteins purified by Ni-NTA affinity chromatography on a HisTrap® FF column (GE Lifescience) on an AKTA™ Avant FPLC (GE Lifescience). The eluate was resolved by SDS-PAGE on acrylamide gels (Bio-Rad) and stained with InstantBlue Ultrafast Coomassie (Sigma-Aldrich). Purity was determined using densitometry of the protein band with ImageLab software (Bio-Rad). Purified endonucleases were dialyzed into a storage buffer composed of 50 mM Tris-HCl, 300 mM NaCl, 1 mM TCEP, 5% glycerol; pH 7.5 and stored at −80° C.

Target DNAs containing spacer sequences and PAM sequences (determined e.g., as in Example 2) were constructed by DNA synthesis. A single representative PAM is chosen for testing when the PAM has degenerate bases. The target DNAs are comprised of 2200 bp of linear DNA derived from a plasmid via PCR amplification with a PAM and spacer located 700 bp from one end. Successful cleavage results in fragments of 700 and 1500 bp. The target DNA, in vitro transcribed single RNA, and purified recombinant protein are combined in cleavage buffer (10 mM Tris, 100 mM NaCl, 10 mM $MgCl_2$) with an excess of protein and RNA and are incubated for 5 minutes to 3 hours, usually 1 hr. The reaction is stopped via addition of RNAse A and incubation at 60 minutes. The reaction is then resolved on a 1.2% TAE agarose gel and the fraction of cleaved target DNA is quantified in ImageLab software.

Example 5.—Activity in E. coli

E. coli lacks the capacity to efficiently repair double-stranded DNA breaks. Thus, cleavage of genomic DNA can be a lethal event. Exploiting this phenomenon, endonuclease activity is tested in E. coli by recombinantly expressing an endonuclease and a guide RNA in a target strain with spacer/target and PAM sequences integrated into its genomic DNA.

For testing of nuclease activity in bacterial cells, BL21 (DE3) strains (NEB) were transformed with plasmids containing T7-driven effector and sgRNA (10 ng each plasmid), plated and grown overnight. The resulting colonies were cultured overnight in triplicate, then subcultured in SOB and grown to OD 0.4-0.6. 0.5 OD equivalent of cell culture was made chemocompetent according to standard kit protocol (Zymo Mix and Go™ kit) and transformed with 130 ng of a kanamycin plasmid either with or without a spacer and PAM in the backbone. After heat shock, transformations were recovered in SOC for 1 hr at 37° C., and nuclease efficiency was determined by a 5-fold dilution series grown on induction media (LB agar plates with antibiotics and 0.05 mM IPTG). Colonies were quantified from the dilution series to measure overall repression due to nuclease-driven plasmid cleavage.

The results for such an assay are shown in FIGS. 12A-12B. FIG. 12A shows replica plating of *E. coli* strains demonstrating plasmid cutting; *E. coli* expressing MG34-1 and a sgRNA were transformed with a kanamycin resistance plasmid containing a target for the sgRNA (+sp). Plate quadrants that show growth impairment (+sp) vs. the negative control (without the target and PAM (−sp)) indicate successful targeting and cleavage by the enzyme. The experiment was replicated twice and performed in triplicate. FIG. 12B shows graphs of colony forming unit (cfu) measurements from the replica plating experiments in A showing growth repression in the target condition (+sp) vs. the non-target control (−sp), demonstrating the plasmid was cut.

Engineered strains with PAM sequences (determined e.g. as in Example 2) integrated into their genomic DNA are transformed with DNA encoding the endonuclease. Transformants are then made chemocompetent and are transformed with 50 ng of guide RNAs (e.g., crRNAs) either specific to the target sequence ("on target"), or non-specific to the target ("non target"). After heat shock, transformations are recovered in SOC for 2 hrs at 37° C. Nuclease efficiency is then determined by a 5-fold dilution series grown on induction media. Colonies are quantified from the dilution series in triplicate.

Example 6.—Testing Genome Cleavage Activity of MG CRISPR Complexes in Mammalian Cells To show targeting and cleavage activity in mammalian cells, the MG Cas effector protein sequences are tested in two mammalian expression vectors: (a) one with a C-terminal SV40 NLS and a 2A-GFP tag, and (b) one with no GFP tag and two SV40 NLS sequences, one on the N-terminus and one on the C-terminus. The NLS sequences comprise any of the NLS sequences described herein. In some instances, nucleotide sequences encoding the endonucleases are codon-optimized for expression in mammalian cells.

The corresponding crRNA sequence with targeting sequence attached is cloned into a second mammalian expression vector. The two plasmids are cotransfected into HEK293T cells. 72 hr after co-transfection of the expression plasmid and a gRNA targeting plasmid into HEK293T cells, the DNA is extracted and used for the preparation of an NGS-library. Percent NHEJ is measured via indels in the sequencing of the target site to demonstrate the targeting efficiency of the enzyme in mammalian cells. At least 10 different target sites are chosen to test each protein's activity.

Example 7.—Predicted Activity of MG Families Described Herein

In situ expression and protein sequence analyses indicate that these enzymes are active nucleases. They contain predicted endonuclease-associated domains (matching RRXRR and HNH endonuclease Pfam domains; FIGS. 2, 3A and 3B), and contain predicted HNH and RuvC catalytic residues (e.g. FIGS. 2, 3A and 3B, rectangles). Furthermore, the presence of an RRXRR motif, found in Ribonuclease H-like protein families, indicates potential RNA targeting and/or nuclease activity (See FIG. 2).

Expression data confirms in situ natural activity for candidate MG34-1 nuclease, tracrRNA and CRISPR array (FIG. 4A-C).

Example 8.—Activity in Mammalian Cells with mRNA Delivery

For genome editing using cell transfection/transformation with mRNA, the coding sequence is mouse or human codon optimized using algorithms from Twist Bioscience or Thermo Fisher Scientific (GeneArt). A cassette is constructed with two nuclear localization signals appended to the coding endonuclease sequence: SV40 and nucleoplasmin at the N and C terminal respectively. Additionally, untranslated regions from human complement 3 (C3) are appended to both the 5' and 3' to the coding sequence within the cassette.

This cassette is then cloned into a mRNA production vector upstream of a long poly A stretch. The mRNA construct organization can be as follows: 5' UTR from C3-SV40 NLS—codon optimized SMART gene—nucleoplasmin NLS—3' UTR from C3-107 polyA tail. Run-of transcription of the mRNA is then driven by a T7 promoter using an engineered T7 RNA polymerase (Hi-T7: New England Biolabs). 5' capping of the mRNA occurs co-transcriptionally using CleanCap® AG (Trilink Biolabs). mRNA is then purified using MEGAclear® Transcription Clean-Up kit (Thermo Fisher Scientific).

Mammalian cells are co-transfected with transcribed mRNA and a set of at least 10 guides targeting a genomic region of interest using Lipofectamine™ Messenger Max (Thermo Fisher Scientific). Cells are incubated for a period of time (e.g. 48 hours) followed by genomic DNA isolation using a Purelink™ Genomic DNA extraction kit (Fisher Scientific). The region of interest is amplified using specific primers. Editing is then assessed by Sanger sequencing using Inxference of CRISPR Edits and NGS for a thorough analysis of edit outcomes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

SEQUENCE LISTING

The patent contains a lengthy sequence listing. A copy of the sequence listing is available in electronic form from the USPTO web site (https://seqdata.uspto.gov/?pageRequest=docDetail&DocID=US11946039B2). An electronic copy of the sequence listing will also be available from the USPTO upon request and payment of the fee set forth in 37 CFR 1.19(b)(3).

What is claimed is:

1. An engineered nuclease system comprising:
   (a) an endonuclease comprising a RuvC-I domain and an HNH domain; and
   (b) an engineered guide ribonucleic acid (RNA) structure capable of forming a complex with said endonuclease comprising:
      (i) a guide RNA sequence capable of hybridizing to a target deoxyribonucleic acid (DNA) sequence; and
      (ii) an RNA sequence capable of binding to said endonuclease, wherein said RNA sequence comprises a sequence with at least 90% sequence identity to nonvariable nucleotides of any one of SEQ ID NOs: 203, 202, 613, or 614,
   wherein said endonuclease comprises a sequence with at least 70% sequence identity to SEQ ID NO: 2.

2. The engineered nuclease system of claim 1, wherein said endonuclease is an archaeal endonuclease.

3. The engineered nuclease system of claim 1, wherein said endonuclease is a class 2, type II Cas endonuclease.

4. The engineered nuclease system of claim 1, wherein said endonuclease further comprises an arginine-rich region comprising an RRxRR motif or a domain with PF14239 homology.

5. The engineered nuclease system of claim 4, wherein said arginine rich region or said domain with PF 14239 homology has at least 85% identity to an arginine rich region or a domain with PF14239 homology of any one of SEQ ID NOs: 1-198, 221-459, 463-612, or 617-668.

6. The engineered nuclease system of claim 1, wherein said endonuclease further comprises a recognition (REC) domain.

7. The engineered nuclease system of claim 6, wherein said REC domain has at least 85% identity to a REC domain of any one of SEQ ID NOs: 1-198, 221-459, 463-612, or 617-668.

8. The engineered nuclease system of claim 1, wherein said endonuclease further comprises a bridge helix (BH) domain, a wedge (WED) domain, and a PAM-interacting (PI) domain.

9. The engineered nuclease system of claim 8, wherein said BH domain, said WED domain, or said PI domain has at least 85% identity to a BH domain, a WED domain, or a PI domain of any one of SEQ ID NOs: 1-198, 221-459, 463-612, or 617-668.

10. The engineered nuclease system of claim 1, wherein said endonuclease has less than 80% identity to a SpCas9 endonuclease.

11. The engineered nuclease system of claim 1, wherein said sequence identity is determined by a BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

12. The engineered nuclease system of claim 1, wherein said endonuclease comprises one or more nuclear localization sequences (NLSs) proximal to an N-terminus of said endonuclease.

13. The engineered nuclease system of claim 1, further comprising a single- or double-stranded DNA repair template comprising from 5' to 3': a first homology arm comprising a sequence of at least 20 nucleotides 5' to said target DNA sequence, a synthetic DNA sequence of at least 10 nucleotides, and a second homology arm comprising a sequence of at least 20 nucleotides 3' to said target DNA sequence.

14. The engineered nuclease system of claim 13, wherein said first homology arm or said second homology arm comprises a sequence of at least 40 nucleotides.

15. The engineered nuclease system of claim 1, wherein said endonuclease comprises a sequence with at least about 85% sequence identity to SEQ ID NO: 2.

16. The engineered nuclease system of claim 1, wherein said endonuclease has a molecular weight of about 120 kDa or less, 100 kDa or less, 90 kDa or less, or 60 kDa or less.

17. The engineered nuclease system of claim 1, wherein said engineered guide RNA structure comprises a single RNA polynucleotide comprising said guide RNA sequence and said RNA sequence capable of binding to said endonuclease.

18. The engineered nuclease system of claim 1, wherein said guide RNA sequence is complementary to a eukaryotic, fungal, plant, mammalian, or human genomic sequence.

19. The engineered nuclease system of claim 1, wherein said guide RNA sequence is 15-24 nucleotides in length.

20. The engineered nuclease system of claim 1, wherein said endonuclease comprises one or more nuclear localization sequences (NLSs) proximal to a C-terminus of said endonuclease.

21. The engineered nuclease system of claim 1, wherein said engineered guide RNA structure comprises an RNA sequence predicted to comprise a hairpin comprising a stem and a loop, wherein said stem comprises at least 12 pairs of ribonucleotides.

22. The engineered nuclease system of claim 21, wherein said engineered guide RNA structure further comprises a second stem and a second loop, wherein said second stem comprises at least 5 pairs of ribonucleotides.

23. The engineered nuclease system of claim 21, wherein said engineered guide RNA structure further comprises an RNA structure comprising at least two hairpins.

24. The engineered endonuclease system of claim 1, wherein said RNA sequence comprises a sequence with at least 95% sequence identity to nucleotides 23-93 of SEQ ID NO: 202, nucleotides 23-157 of SEQ ID NO: 203, nucleotides 23-145 of SEQ ID NO: 613, or nucleotides 23-157 of SEQ ID NO: 614.

* * * * *